US012690908B2

(12) United States Patent
Stefater, III et al.

(10) Patent No.: US 12,690,908 B2
(45) **Date of Patent: *Jul. 28, 2026**

(54) METHODS OF ALLEVIATING SYMPTOMS OF OCULAR SURFACE DISCOMFORT USING MEDICAL ICE SLURRY

(71) Applicant: EyeCool Therapeutics, Inc., Cambridge, MA (US)

(72) Inventors: James Anthony Stefater, III, Boston, MA (US); Tomasz Pawel Stryjewski, Somerville, MA (US); Sameer Sabir, Arlington, MA (US)

(73) Assignee: EYECOOL THERAPEUTICS, INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/546,158

(22) Filed: Feb. 20, 2026

(65) Prior Publication Data

US 2026/0183039 A1 Jul. 2, 2026

Related U.S. Application Data

(63) Continuation of application No. 18/948,163, filed on Nov. 14, 2024, which is a continuation of application
(Continued)

(51) Int. Cl.
*A61B 18/02* (2006.01)
*A61F 7/00* (2006.01)
(Continued)

(52) U.S. Cl.
CPC ................ *A61B 18/02* (2013.01); *A61F 7/10* (2013.01); *A61K 9/0048* (2013.01); *A61K 9/10* (2013.01);
(Continued)

(58) Field of Classification Search
CPC . A61B 18/02; A61B 2018/00327; A61F 7/10; A61F 2007/0004; A61F 2007/0056;
(Continued)

(56) References Cited

U.S. PATENT DOCUMENTS 2,101,628 A 12/1937 Padelford
2,313,282 A 3/1943 Tunke
(Continued)

FOREIGN PATENT DOCUMENTS

CN 106214325 A 12/2016
CN 106344397 A 1/2017
(Continued)

OTHER PUBLICATIONS

"Anesthesia for Eye Surgery: On Improving Retinal Anesthesia Technology," Bold Business article, Mar. 2, 2018 (https://www.Boldbusiness.Com/Health/Anesthesia-For-Eye-Surgery-Technology) (8 pages).
(Continued)

*Primary Examiner* — Jessica Arble
(74) *Attorney, Agent, or Firm* — Wilmer Cutler Pickering Hale and Dorr LLP

(57) ABSTRACT

Disclosed herein is a method of alleviating symptoms of ocular surface discomfort, the method comprising: topically applying a cold slurry adjacent to a corneal limbus of an eye of a patient, wherein the cold slurry comprises water and a freezing point depressant, wherein the topical application of the cold slurry is configured to cause a degree of numbing of a cornea of the eye for a period of time, and wherein an ocular sensation of the eye is restored following the period of time.

20 Claims, 11 Drawing Sheets

Related U.S. Application Data

No. 18/907,345, filed on Oct. 4, 2024, which is a continuation of application No. 18/299,444, filed on Apr. 12, 2023, now abandoned, which is a continuation of application No. 17/839,674, filed on Jun. 14, 2022, now Pat. No. 11,653,969, which is a continuation of application No. 17/439,749, filed as application No. PCT/US2021/024514 on Mar. 26, 2021, now Pat. No. 11,399,882.

(60) Provisional application No. 63/000,922, filed on Mar. 27, 2020.

(51) Int. Cl.

| *A61F 7/02* | (2006.01) |
| *A61F 7/10* | (2006.01) |
| *A61K 9/00* | (2006.01) |
| *A61K 9/10* | (2006.01) |
| *A61K 47/10* | (2017.01) |
| *A61M 19/00* | (2006.01) |
| *G02C 5/00* | (2006.01) |
| *A61B 18/00* | (2006.01) |

(52) U.S. Cl.
CPC ............. *A61K 47/10* (2013.01); *A61M 19/00* (2013.01); *G02C 5/001* (2013.01); *A61B 2018/00327* (2013.01); *A61F 2007/0004* (2013.01); *A61F 2007/0056* (2013.01); *A61F 2007/0285* (2013.01)

(58) Field of Classification Search
CPC . A61F 2007/0285; A61K 9/0048; A61K 9/10; A61K 47/10; A61M 19/00; G02C 5/001
See application file for complete search history.

(56) References Cited

U.S. PATENT DOCUMENTS

| 2,796,903 | A | 6/1957 | Gazelle |
| 3,762,419 | A | 10/1973 | Walters |
| 4,068,918 | A | 1/1978 | Holcombe, Jr. |
| 4,243,041 | A | 1/1981 | Paul |
| 5,190,033 | A | 3/1993 | Johnson |
| 5,368,590 | A | 11/1994 | Itoh |
| 5,514,094 | A | 5/1996 | Anello et al. |
| 5,953,097 | A | 9/1999 | Stark |
| 6,099,521 | A | 8/2000 | Shadduck |
| 6,241,711 | B1 | 6/2001 | Weissberg et al. |
| 6,409,746 | B1 | 6/2002 | Igaki et al. |
| 6,824,556 | B1 | 11/2004 | Lachance |
| 7,930,772 | B2 | 4/2011 | Fontanez |
| 8,257,256 | B1 | 9/2012 | Krolman |
| 8,262,715 | B2 | 9/2012 | Wong, Jr. et al. |
| 8,439,960 | B2 | 5/2013 | Burnett et al. |
| 8,992,516 | B2 | 3/2015 | Muller |
| 9,144,513 | B2 | 9/2015 | Paulson |
| D787,694 | S | 5/2017 | Baltazar |
| 9,956,355 | B2 | 5/2018 | Besirli et al. |
| 10,201,471 | B2 | 2/2019 | Yang |
| 10,238,814 | B2 | 3/2019 | Besirli et al. |
| 10,322,248 | B2 | 6/2019 | Besirli et al. |
| 10,369,056 | B2 | 8/2019 | Paulson |
| 10,420,674 | B2 | 9/2019 | Johnson |
| 11,241,330 | B1 | 2/2022 | Sabir et al. |
| 11,399,882 | B2 | 8/2022 | Stefater, III et al. |
| 11,471,401 | B2 | 10/2022 | Garibyan et al. |
| D968,627 | S | 11/2022 | Kim |
| 11,564,830 | B2 | 1/2023 | Garibyan et al. |
| 11,653,969 | B2 | 5/2023 | Stefater, III et al. |
| 2002/0049389 | A1 | 4/2002 | Abreu |
| 2004/0249427 | A1 | 12/2004 | Nabilsi |
| 2005/0120734 | A1 | 6/2005 | Yon |
| 2007/0282282 | A1* | 12/2007 | Wong, Jr. ............... A61N 1/306 604/294 |
| 2008/0148769 | A1 | 6/2008 | Higgins |
| 2009/0275936 | A1 | 11/2009 | Muller |
| 2011/0307041 | A1 | 12/2011 | Floyd |
| 2013/0158637 | A1 | 6/2013 | Sheikh |
| 2014/0025144 | A1 | 1/2014 | Ragan |
| 2014/0081361 | A1 | 3/2014 | Dhayan |
| 2015/0165231 | A1 | 6/2015 | Scheja et al. |
| 2016/0000600 | A1 | 1/2016 | Lee |
| 2016/0279350 | A1 | 9/2016 | Besirli et al. |
| 2017/0231816 | A1 | 8/2017 | Ryan |
| 2017/0274011 | A1 | 9/2017 | Garibyan et al. |
| 2017/0304558 | A1 | 10/2017 | Besirli et al. |
| 2017/0368298 | A1 | 12/2017 | Bojanova |
| 2018/0289533 | A1 | 10/2018 | Johnson et al. |
| 2019/0015602 | A1 | 1/2019 | Besirli et al. |
| 2019/0053939 | A1 | 2/2019 | Garibyan et al. |
| 2019/0125579 | A1 | 5/2019 | Habib |
| 2019/0167916 | A1 | 6/2019 | Besirli et al. |
| 2019/0328753 | A1 | 10/2019 | Yee et al. |
| 2020/0054483 | A1 | 2/2020 | Kim |
| 2020/0100934 | A1 | 4/2020 | Ariano et al. |
| 2020/0163797 | A1 | 5/2020 | Besirli et al. |
| 2020/0206023 | A1 | 7/2020 | Pathak et al. |
| 2020/0215144 | A1 | 7/2020 | Yang |
| 2021/0007882 | A1 | 1/2021 | Kim |
| 2021/0145500 | A1* | 5/2021 | Barken .................. A61B 18/02 |
| 2022/0218514 | A1 | 7/2022 | Azar et al. |
| 2024/0207183 | A1 | 6/2024 | Sabir et al. |

FOREIGN PATENT DOCUMENTS

| CN | 106691685 | A | 5/2017 |
| CN | 107280854 | A | 10/2017 |
| CN | 107736962 | A | 2/2018 |
| CN | 107773350 | A | 3/2018 |
| CN | 108272549 | A | 7/2018 |
| CN | 108524098 | A | 9/2018 |
| CN | 108743030 | A | 11/2018 |
| CN | 108814802 | A | 11/2018 |
| CN | 108815584 | A | 11/2018 |
| CN | 109077909 | A | 12/2018 |
| CN | 109077947 | A | 12/2018 |
| CN | 110025463 | A | 7/2019 |
| CN | 110215335 | A | 9/2019 |
| CN | 110279517 | A | 9/2019 |
| CN | 110393623 | A | 11/2019 |
| CN | 110393624 | A | 11/2019 |
| CN | 110433272 | A | 11/2019 |
| CN | 110755193 | A | 2/2020 |
| CN | 110809457 | A | 2/2020 |
| CN | 110882103 | A | 3/2020 |
| CN | 111096846 | A | 5/2020 |
| CN | 111297557 | A | 6/2020 |
| CN | 217366288 | U | 9/2022 |
| CN | 115957067 | A | 4/2023 |
| CN | 116439904 | A | 7/2023 |
| DE | 29712559 | U1 | 9/1997 |
| DE | 202013102909 | U1 | 9/2013 |
| DE | 202015102909 | U1 | 7/2015 |
| FR | 2909545 | A1 | 6/2008 |
| GB | 2537833 | A | 11/2016 |
| JP | H0661224 | U | 8/1994 |
| JP | 2007-511293 | A | 5/2007 |
| JP | 2017-526684 | A | 9/2017 |
| JP | 2019-506248 | A | 3/2019 |
| KR | 1020060084878 | A | 7/2006 |
| KR | 200422938 | Y1 | 8/2006 |
| KR | 2020100002818 | U | 3/2010 |
| KR | 2020100009316 | U | 9/2010 |
| KR | 20100107157 | A | 10/2010 |
| KR | 101107942 | B1 | 1/2012 |
| KR | 20130007077 | A | 1/2013 |
| KR | 101486160 | B1 | 1/2015 |
| KR | 101544610 | B1 | 8/2015 |
| KR | 101827457 | B1 | 2/2018 |
| KR | 101851179 | B1 | 4/2018 |
| MX | PA06005434 | A | 1/2007 |

(56) References Cited

FOREIGN PATENT DOCUMENTS

| WO | WO-2001/039704 A1 | 6/2001 |
|----|-------------------|--------|
| WO | WO-2005/049071 A2 | 6/2005 |
| WO | WO-2007/102362 A1 | 9/2007 |
| WO | WO-2010/039117 A1 | 4/2010 |
| WO | WO-2015/011455 A1 | 1/2015 |
| WO | WO-2015/149536 A1 | 10/2015 |
| WO | WO-2015/149537 A1 | 10/2015 |
| WO | WO-2016/010355 A1 | 1/2016 |
| WO | WO-2016/033384 A1 | 3/2016 |
| WO | WO-2017/147367 A1 | 8/2017 |
| WO | WO-2018/160797 A1 | 9/2018 |
| WO | WO-2018/225913 A1 | 12/2018 |
| WO | WO-2020/117030 A1 | 6/2020 |
| WO | WO-2021/016457 A1 | 1/2021 |
| WO | WO-2022/261494 A1 | 12/2022 |
| WO | WO-2023/154902 A1 | 8/2023 |
| WO | WO-2023/215407 A2 | 11/2023 |
| WO | WO-2024/163973 A1 | 8/2024 |

OTHER PUBLICATIONS

Alcaine—proparacaine hydrocholoride solution/drops, Alcon Laboratories, Inc., 2020 (6 pages).

Andreoli, C. M., et al. Open globe injuries: Emergent evaluation and initial management, In: UpToDate, Post TW (Ed), Up To Date, Waltham, MA (Literature review current through Aug. 2021; topic last updated Feb. 2020) (38 pages).

Belmonte, C., et al., "Sensory Innervation of the Eye", Chapter 16, Adler's Physiology of the Eye (Eleventh Edition), pp. 363-384, 2011, Elsevier Inc. (22 pages).

Benson, M. T., et al., "Cyclocryotherapy: a review of cases over a 10-year period," British Journal of Ophthalmology, 1990, 74, pp. 103-105 (3 pages).

Besirli, Cagri G., et al., Randomized Safety and Feasiblity Trial of Ultra-Rapid Cooling Anesthesia for Intravitreal Injections, Ophthalmol Retina, Apr. 15, 2020; S2468-6530(20)30142-1, doi: 10.1016/j.oret.2020.04.001 (2 pages).

Bras, Alvaro, et al., "Safety Alert: Risks associated with Ophthalmic Anesthetics," reviewed by Dr. S. Brodovsky, MD, FRCSC, WRHA Pharmacy Program, Sep. 2016 (4 pages).

Chao, Daniel L., et al., A Novel Rapid Cooling Device for Intravitreal Injection Anesthesia: Results of the Prospective COOL-2 Study, Investigative Ophthalmology & Visual Sicence, vol. 61, 4196, ARVO Annual Meeting Abstract, Jun. 2020 (2 pages).

Chee, C. K. L., et al., "Cyclocryotherapy for chronic glaucoma after vitreoretinal surgery," Eye 8, pp. 414-418, 1994 (5 pages).

Heiting, G., Cornea of the eye. All About Vision, 2017 (retrieved from https://www.allaboutvision.com/resources/cornea.htm) (7 pages).

International Search Report and Written Opinion of the International Searching Authority, mailed Jul. 8, 2021, for International Application No. PCT/US2021/024514 (8 pages).

Kim, Byoung Seon, et al., "Long term Results from Cyclocryotherapy Applied to the 3O'clock and 9O'clock Positons in Blind Refractory Glaucoma Patients," Korean J Ophthalmol 2015; 29(1): 47-52, doi 10.3341/kjo.2015.29.1.47 (6 pages).

Lee, B. S., et al., "Managing dry eye disease and facilitating realistic patient expectations: A review and appraisal of current therapies," Clinical Ophthalmology 2020, 14: 119-126, published online Jan. 14, 2020, doi: 10.2147/OPTH.S228838 (8 pages).

Levitt, A E., et al., "Chronic dry eye symptoms after LASIK: parallels and lessons to be learned from other persistent post-operative pain disorders," Molecular Pain (2015), 11 :21, doi 10.1186/s12990-015-0020-7 (12 pages).

Lindsell, Lucas B., et al., "Use of Topical Ice for Local Anesthesia for Intravitreal Injections," JAMA Ophthalmology, Aug. 2014, vol. 132, No. 8, pp. 1010-1011 (2 pages).

Mcmonnies, C. W., "The potential role of neuropathic mechanisms in dry eye syndromes," Journal of Optometry (2017), 10, 5-13, doi: http://dx.doi.org/10.1016/j.optom.2016.06.002 (9 pages).

Mcmonnies, C. W., The potential role of neuropathic mechanisms in dry eye syndromes, Journal of Optomertry, 2016, ttp://dx.doi.org/10.1016/j.optom.2016.06.002 (9 pages).

NDA 208135: Tetracaine hydrochloride ophthalmic solution, FDA, Apr. 30, 2015 (26 pages).

Pathak, A. K., et al., Pain reduction after photoablation. EyeWiki by the American Academy of Ophthalmology, 2019 (2 pages).

Recens Medical, Inc., "Cooling Anesthesia for Intravitreal Injection (COOL-1)," ClinicalTrials.gov Identifier: NCT03732287, First Posted Nov. 6, 2018 (7 pages).

Shah, Anjali, "Cryoanesthesia for Intravitreal Injections," NCT02872012, Protocol Version 4.0, Oct. 11, 2017 (15 pages).

Shetty, R., et al., "Pain management after photorefractive keratectomy," Journal of Cataract & Refractive Surgery, vol. 45, Issue 7, pp. 972-976, Jul. 2019, doi: 10.1016/j .jcrs2019.01.032 (5 pages).

Sowka, Joseph et al., "Just an Eyedrop? Think Again," Review of Optometry, vol. 143:03, Issue: Mar. 15, 2006, published May 3, 2006 (3 pages).

Spierer, Oriel, et al. "Corneal mechanical thresholds negatively associate with dry eye and ocular pain symptoms," Investigative Ophthalmolgy & Visual Science, vol. 57, 617-625, Feb. 2016 , doi: 10.1167/iovs.15-18133 (9 pages).

Sridhar, M. S., "Anatomy of cornea and ocular surface.," Indian Journal of Ophthalmology, 66(2), 190-194, Feb. 2018, doi: 10.4103/ijo.IJO _ 646 _ 17 (13 pages).

Video: Dr. Najeeb Lectures, Ciliary Ganglion—Gross Anatomy, https://www.youtube.com/watch?v=6kH6Fg7ES6E), posted Jun. 6, 2014 (7 pages).

Video: Soton Brain Hub, The Ciliary Ganglion, https://www.youtube.com/watch?v=kQiP-zuNEHA, posted Aug. 8, 2015 (3 pages).

Zarei-Ghanavati, S., et al., "Efficacy of corneal cooling on postoperative pain management after photorefractive keratectomy: A contralateral eye randomized clinical trial," Journal of Current Ophthalmology, vol. 29, Issue 4, pp. 264-269, Dec. 2017, doi: 10.1016/j .joco.2017.04.004 (6 pages).

Olson, J. and Stravino, V., "A Review of Cryotherapy," Physical Therapy, vol. 52, No. 8, pp. S40-S53 (Aug. 1972).

Cataldi, J.K., et al., "Cryotherapy Effects, Part 2: Time to Numbness Onset and Numbness Duration," International Journal of Athletic Therapy & Training, vol. 18, No. 5, pp. 26-28 (Sep. 2013).

Attia, A.A.M. and Hassan, A.M., "Effect of cryotherapy on pain management at the puncture site of arteriovenous fistula among children undergoing hemodialysis," International Journal of Nursing Sciences, vol. 4, pp. 46-51 (available online Dec. 18, 2016).

Fraunfelder, F., "Liquid Nitrogen Cryotherapy for Surface Eye Disease (An AOS Thesis)," Transactions of the American Ophthalmological Society, vol. 106, pp. 301-324 (46 total pages), PMCID: PMC2646430, PMID: 19277243 (2008).

Morkin, M.I. and Hamrah, P., "Efficacy of Self-Retained Cryopreserved Amniotic Membrane for Treatment of Neuropathic Corneal Pain," The Ocular Surface, vol. 16, Issue 1, pp. 132-138 (Author Manuscript—25 total pages), retrieved from https://www.sciencedirect.com/science/article/pii/S1542012417302264 (Jan. 2018).

Reitberger, H.H., et al., "Argon cold plasma—a novel tool to treat therapy-resistant corneal infections," American Journal of Ophthalmology, doi: 10.1016/j.ajo.2018.03.025, Author Manuscript—27 total pages (Accepted Mar. 14, 2018).

Shetty, R., et al., "Cold bandage contact lens use reduces post-photorefractive keratectomy or corneal collagen-crosslinking pain perception in patients," Indian Journal of Ophthalmology, vol. 71, No. 5, pp. 1885-1861 (20 total pages), May 2023.

International Search Report and Written Opinion issued Jun. 21, 2024 by U.S. Patent and Trademark Office as International Searching Authority for International Bureau of WIPO in International Patent Application No. PCT/US2024/014354 (12 total pages).

Office Action issued by China National Intellectual Property Administration on May 29, 2025 in Chinese Patent Application No. 202180024320.9 with partial English translation (15 total pages).

Office Action issued Sep. 5, 2025 by China National Intellectual Property Administration in Chinese Patent Application No. 202180024320.9 with partial English translation (17 total pages).

Final Office Action issued Sep. 17, 2025 by U.S. Patent and Trademark Office in U.S. Appl. No. 19/048,089 (9 total pages).

(56)         References Cited

OTHER PUBLICATIONS

Final Office Action issued Jul. 29, 2025 by U.S. Patent and Trademark Office in U.S. Appl. No. 18/948,163 (11 total pages).

\* cited by examiner

| ICE PERCENTAGE CALCULATIONS | | |
|---|---|---|
| Mixture: | Value | Units |
| Volume normal saline | 80 | mL |
| Volume Glycerol | 20 | mL |
| Temperature setpoint | -10 | °C |
| Mass H20 | 79.6 | g |
| Mass NaCl | 0.72 | g |
| % Glycerol | 20% | L/L solution |
| Mass Glycerol | 25.2 | g |
| Ice percentage | 30% | ice by mass |

FIG. 2

Sclera

Cornea

Limbus

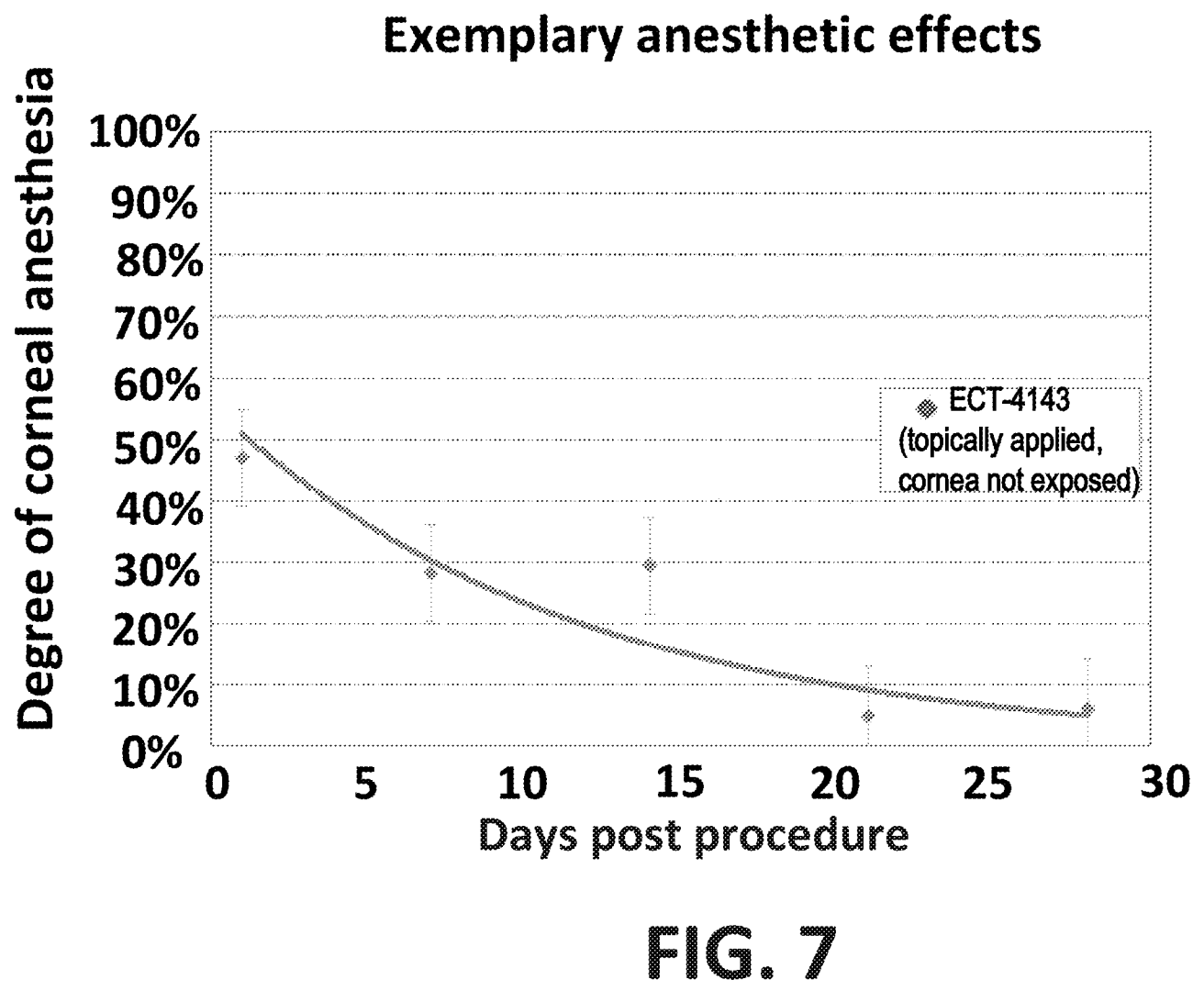

Exemplary anesthetic effects

ECT-4143
(topically applied,
cornea not exposed)

Days post procedure

Degree of corneal anesthesia

FIG. 7

Control, n=3
(example #44)

Start

Average healing rate:
1.31 mm²/hour 24 hours

Average healing
rate: 0.62 mm²/hour 60 hours

ECT-4143
treated, n=3
(Example #47)

Start

Average healing rate:
1.09 mm²/hour 24 hours

Average healing rate:
0.63 mm²/hour 60 hours

METHODS OF ALLEVIATING SYMPTOMS OF OCULAR SURFACE DISCOMFORT USING MEDICAL ICE SLURRY

TECHNICAL FIELD

This application is a continuation of U.S. application Ser. No. 18/948,163 filed on Nov. 14, 2024, which is a continuation of U.S. application Ser. No. 18/907,345 filed on Oct. 4, 2024, which is a continuation of U.S. application Ser. No. 18/299,444, filed on Apr. 12, 2023, which is a continuation of U.S. application Ser. No. 17/839,674, filed on Jun. 14, 2022, now U.S. Pat. No. 11,653,969, which is a continuation of U.S. application Ser. No. 17/439,749, filed on Sep. 15, 2021, now U.S. Pat. No. 11,399,882, which is a national stage application of International Application No. PCT/US2021/024514, entitled "METHODS OF ALLEVIATING SYMPTOMS OF OCULAR SURFACE DISCOMFORT USING MEDICAL ICE SLURRY," filed on Mar. 26, 2021, which claims the benefit of and priority to U.S. Provisional Patent Application No. 63/000,922, filed on Mar. 27, 2020, the disclosures of each of which are hereby incorporated by reference in their entireties. The present invention relates generally to apparatuses, systems, and methods for creating and administering a biomaterial such as a cold slurry. More particularly, the present invention relates to systems and methods for treating ocular surface discomfort by administering a cold slurry to a subject to cause ocular hypesthesia in a safe and effective manner.

BACKGROUND

The cornea of the eye is a transparent, avascular tissue that measures approximately 11-12 mm horizontally and 9-11 mm vertically. Sridhar, M. S., Anatomy of cornea and ocular surface. *Indian Journal of Ophthalmology*, 66(2), 190-194 (February 2018). It is located on the outermost surface of the eye, positioned in front of the pupil and iris, in order to refract light as it enters.

Innervation to the cornea begins at the brain stem, where a large sensory root branches off the pons and attaches to the trigeminal nucleus caudalis—located at the lateral portion of the medulla. From there, the trigeminal nerve branches off into three divisions, one of which is the ophthalmic division. This root divides into three more branches, with one extension, called the nasociliary nerve. This purely sensory nerve travels along the superior portion of the orbital cavity and contributes smaller branches to the cornea. The two types of divisions from this nerve are called short ciliary nerves and long ciliary nerves. The short ciliary nerves pass through a sensory root, into the ciliary ganglion, then exit that nucleus to pierce the sclera and enter the peri-choroidal space, where they can move into the cornea. Belmonte, C., Tervo, T. T., & Gallar, J. (2011). CHAPTER 16-Sensory Innervation of the Eye. *Adler's Physiology of the Eye* (Eleventh Edition, pp. 363-384). Elsevier Inc.

The peri-choroidal space is located between the sclera, the outermost layer of the eyeball, and the choroid, the heavily vasculated layer that is responsible for providing nutrients to the structures of the eye. There are about 8-10 short ciliary nerves that puncture the sclera, but these nerves branch into about 15-20 divisions once inside the peri-choroidal space. In regard to the long ciliary nerves, there are over 50 branches that pierce the sclera and divide again inside the peri-choroidal space. At the limbus, the junction between the sclera and cornea, the nerves lose their myelin sheath and continue as free nerve endings. The nerves collect sensory signals from the cornea and send them backwards, towards the brain stem. Belmonte, C., Tervo, T. T., & Gallar, J. (2011). CHAPTER 16-Sensory Innervation of the Eye. *Adler's Physiology of the Eye* (Eleventh Edition, pp. 363-384). Elsevier Inc. Not all the details of corneal innervation are entirely well-understood and may vary somewhat patient to patient. There may be some contribution from other nerve fibers or some normal anatomical variations in the routes of innervation.

The free nerve endings are located under the corneal epithelium, the anterior layer protecting the corneal structure, and often contribute to painful ocular sensations. When patients are bothered by these symptoms, the condition is termed dry eye syndrome (DES), also known as ocular surface disease (OSD). Causes of this condition are multifactorial. One important cause is inadequate amounts of aqueous tear production, causing the eye to lack hydration and lubrication. Other causes of ocular surface disease can include meibomian gland dysfunction or damage to the corneal epithelium.

These "dry eye-induced alterations to the properties of corneal afferent neurons and the central processing of corneal input may have significant consequences for both the regulation of tearing and ocular pain." Mcmonnies, C. W., The potential role of neuropathic mechanisms in dry eye syndromes, *Journal of Optometry*, 10, 5-13 (2017). Importantly, some patients continue to have ocular surface pain even though their ocular surface returns to a clinically normal appearance. This situation presents a clinical challenge because the cause is thought to be somatosensory dysfunction of the corneal innervation that persists long after the original insult that excited the nerves.

Other sources of corneal discomfort can include postoperative pain, potentially after photorefractive keratectomy, which is a procedure used to treat refractive error that requires removal of the corneal epithelium before applying excimer laser ablation. Other surgical procedures can also lead to corneal discomfort, including procedures that do not necessarily involve removal of the epithelium, but where the epithelium undergoes a mild to moderate desiccation during the procedure. A patient can also experience ocular discomfort following ocular trauma (e.g., corneal abrasions) and laser in-situ keratomileusis (LASIK) surgery.

There are three different types of nociceptive receptors innervating the cornea. Twenty percent of corneal nociceptors are Ad mechanoreceptors, which are responsible for fast-conducting sharp, painful stimuli, caused by aggravation to the ocular surface. Seventy percent of corneal nociceptors are polymodal, which are stimulated by corneal nerve damage and cause neuropathic pain and "reflexive tearing." Levitt, A. E., et al., Chronic dry eye symptoms after LASIK: parallels and lessons to be learned from other persistent post-operative pain disorders, Molecular Pain, 11:21 (2015). The last ten percent of corneal nociceptors are C-fiber cold receptors, which play a crucial role in maintaining basal tear secretion. These receptors are highly sensitive to temperature change within corneal tissue, and LASIK surgery can cause evaporation of tears on the tear film surface, lowering the temperature by about 0.3 degrees per second, thus influencing C-fiber signals. (Levitt et al., 2015).

Many mechanisms, including dryness, prior surgery, dysfunction of the eyelid glands, or prior chemical irritation, may lead to the clinical syndrome of OSD, notable for signs of ocular irritation and symptoms characterized as dryness, burning, or discomfort. Even after the initial insult for the mechanism has resolved, i.e. normal lubrication of the eye has been restored, patients may still report significant symptoms of ocular surface discomfort, despite their ocular surface having only minimal signs of disease, suggesting a component of hypersensitization or allodynia. Indeed, literature references note "the status of the ocular surface alone is not sufficient to understand dry eye and that corneal somatosensory function . . . must be considered when evaluating a patient with dry eye." Spierer O, Felix E R, McClel-lan A L, et al. Corneal mechanical thresholds negatively associate with dry eye and ocular pain symptoms. *Invest Ophthalmol Vis Sci.* 57:617-625 (2016). This situation presents a quandary for the treating physician—the patient has residual pain and discomfort with a normal appearing ocular surface (corneal somatosensory dysfunction). Additional lubrication and other therapies targeted to improve the ocular surface are, as expected, no longer of any help to these patients.

Current treatment methods for pain associated with dry eye syndrome/ocular surface disease, PRK, or LASIK surgery, or corneal somatosensory dysfunction are either limited, of transient value, or associated with negative side effects. Dry eye syndrome is most commonly treated with warm compresses, over-the-counter artificial tears, or prescription eye drops targeting improved tear production or reducing inflammation. Physicians may also recommend topical ocular lubricants, hygiene products that clear debris from underneath the eyelids. These methods work by softening meibum, the oily, lipid-rich secretion from meibomian glands, in order to help spread tear production over the cornea. The limitation to these therapies is the short-term relief and need for continuous application. Lubricants or artificial tears may soothe irritation, but do not actually address the cause of dry eye and may also contribute to increased debris collecting under the eyelid. Shen Lee, B., et al., Managing dry eye disease and facilitating realistic patient expectations: A review and appraisal of current therapies, *Clinical Ophthalmology,* 14 119-126 (January 2020).

Regarding postoperative pain management for photorefractive keratectomy and LASIK eye surgery, topical NSAIDs and soft bandage contact lenses are the most common treatment. NSAID medications prevent the production of prostaglandin, a hormone-like substance involved in inflammation, that occurs with corneal tissue damage. Pathak, A. K., & Karacal, H., (2019). Pain reduction after photoablation. *EyeWiki by the American Academy of Ophthalmology.* Topical NSAIDs carry a risk of corneal damage, such as erosions, defects, delayed corneal epithelial healing, or corneal melting (which can lead to vision loss). With soft bandage contact lenses, this method can stimulate the regrowth of epithelial cells, and act as a delivery system for antibiotics or topical NSAIDs. However, bandage contact lenses can promote bacterial growth and are often not be efficient in relieving pain. Shetty, R., et al., Pain management after photorefractive keratectomy, Journal of Cataract Refract Surgery, 45(7): 972-976 (2019).

Acute ocular pain can also be treated with topical ophthalmic anesthetic drops, such as Proparacaine Hydrochloride and Tetracaine Hydrochloride. These aqueous solutions are given as short-term treatment for pain, or when measuring intra-ocular pressure, removing foreign bodies, soothing sutures in the cornea, or as a preoperative anesthetic for ophthalmic surgery. Topical anesthetics can block corneal nerves from sending painful stimuli for about 15-20 minutes per dose. With this short-term pain relief, patients require continuous application, but chronic use can eventually lead to corneal toxicity. Toxic effects on the cornea include damaging stromal keratocytes, which are cells that play a significant role in healing trauma to the cornea. If epithelial cells cannot migrate across the cornea, the epithelium will eventually start to slough off and lead to chronic non-healing of corneal epithelium.

Maintaining some perception of pain, however, is critical to the normal function of the healthy cornea. Neuropathic keratopathy, also known as neurotrophic keratitis, is a syndrome where due to a pathological lack of sensation of the corneal and conjunctiva, the ocular surface experiences a syndrome that progresses from tear film abnormalities, to epitheliopathy, to eventual stromal lysis. For true neuropathic keratopathy, an eye must have a lack of sensation of the cornea and conjunctiva due to pathological destruction to the trigeminal nerve, which can occur from surgery intended to treat trigeminal neuralgias, surgery of acoustic neuromata, or from infections such as herpes zoster ophthalmicus or leprosy. Other forms of neuropathic keratopathy occur from the misuse of topical anesthetics. In rabbit models, typical trophic changes in the corneal epithelium have been shown after controlled thermocoagulation of the trigeminal ganglion in rabbits. This denervation was found to markedly affect the proliferative activity of the epithelium, and mitosis was sparse.

As explained above, the cornea is exquisitely sensitive to pain or perturbation. There are a host of human clinical conditions that cause mild to severe corneal pain and discomfort, all of which could potentially be addressed by the development of a safe and efficacious treatment for corneal pain. The current state of topical numbing drops only numb the cornea for a matter of minutes and chronic use is associated with severe morbidities including corneal infections and corneal melting. Further, traditional approaches for treating ocular pain result in complete anesthesia of sensation to the eye, which can be very problematic in the chronic context due to the risk of development of neuropathic keratopathy. Furthermore, in eyes that are chronically inflamed and painful, a corneal somatosensory dysfunction becomes the predominant feature of the pain syndrome. In summary, there are many patients with debilitating ocular surface discomfort that can be associated with active corneal pathology or can persist long after the original injury with no detectable ongoing pathology. Clearly there is a large unmet clinical need for development of a longer-acting safe corneal anesthetic therapy that partially blocks corneal sensation and significantly decreases patient discomfort.

SUMMARY

In one aspect, the invention provides for a method of alleviating symptoms of ocular surface discomfort, the method comprising: topically applying a cold slurry adjacent to a corneal limbus of an eye of a patient, wherein the cold slurry comprises water and a freezing point depressant, wherein the topical application of the cold slurry is configured to cause a degree of numbing of a cornea of the eye for a period of time, and wherein an ocular sensation of the eye is restored following the period of time.

In some embodiments, the cold slurry is applied posterior to the corneal limbus.

In some embodiments, the period of time is more than about 2 days without topically applying the cold slurry an additional time on any day following the first day of topical application.

In some embodiments, the period of time is more than about 7 days without topically applying the cold slurry an additional time on any day following the first day of topical application.

In some embodiments, the freezing point depressant is glycerol.

In some embodiments, the ocular sensation of the eye is restored after about 21 days following the topical application of the cold slurry.

In some embodiments, a sclera of the eye of the patient is cooled to a temperature of between about –6° C. and about 4° C. during the topical application of the cold slurry.

In some embodiments, the cold slurry is topically applied for between about 5 minutes and about 15 minutes.

In some embodiments, an additional amount of the cold slurry is topically re-applied at about every 90 seconds.

In some embodiments, the method further comprises placing a contact lens on the eye of the patient prior to topically applying the cold slurry.

In some embodiments, the cold slurry is configured to be a paste consistency.

In another aspect, the invention provides for a method of alleviating symptoms of ocular surface discomfort, the method comprising: placing a protective covering over a cornea of an eye of a patient; and topically applying a cold slurry to a bulbar conjunctiva of the eye of the patient, wherein the topical application of the cold slurry causes a prolonged reduction of pain of the eye of the patient, and wherein a partial sensation of the cornea of the eye of the patient is maintained during the prolonged reduction of pain.

In some embodiments, the cold slurry is applied posterior to the corneal limbus.

In some embodiments, the cold slurry is applied over the protective covering.

In some embodiments, the prolonged reduction of pain lasts more than about 7 days without topically applying the cold slurry an additional time on any day following the first day of topical application.

In some embodiments, the prolonged reduction of pain lasts more than about 2 days without topically applying the cold slurry an additional time on any day following the first day of topical application.

In some embodiments, the prolonged reduction of pain lasts more than about 14 days without topically applying the cold slurry an additional time on any day following the first day of topical application.

In some embodiments, the symptoms are due to dry eye syndrome or corneal somatosensory dysfunction.

In some embodiments, a sclera of the eye of the patient is cooled to a temperature of between about –6° C. and about 4° C. during the topical application of the cold slurry.

In some embodiments, the protective covering is a contact lens, and wherein the contact lens prevents the cornea of the eye from freezing.

In another aspect, the invention provides for a method of alleviating symptoms of ocular surface discomfort, the method comprising: administering a cold slurry to an eye of a patient, wherein the cold slurry comprises water and a percentage of ice particles, wherein the administration of the cold slurry causes a prolonged hypesthesia of the eye, wherein an ocular sensation of the eye is restored following the prolonged hypesthesia, and wherein the administration of the cold slurry does not cause permanent damage to a cornea of the eye.

In some embodiments, the method further comprises treating a condition selected from the group consisting of dry eye syndrome, chronic eye pain, post-operative pain, post-photorefractive keratectomy pain, post-LASIK pain, post-cataract surgery pain, and post open globe injury repair pain, post-corneal injury, corneal somatosensory dysfunction, allodynia, and pain from acute injury.

In some embodiments, the cold slurry is administered via injection.

In some embodiments, the cold slurry is injected into a subconjunctival space.

In some embodiments, the cold slurry is administered via topical application.

In some embodiments, the percentage of ice particles is between about 20% and 40%.

In some embodiments, the temperature of the cold slurry is between about –20° C. and about –5° C.

In another aspect, the invention provides for a method of alleviating symptoms of ocular surface discomfort, the method comprising: topically applying a cold slurry on or proximal to an ocular surface of an eye of a patient, wherein the topical application of the cold slurry causes a prolonged hypesthesia of a cornea of the eye, wherein an ocular sensation of the eye is restored following the prolonged hypesthesia, and wherein the topical application of the cold slurry does not cause permanent damage to the cornea of the eye.

In some embodiments, the cold slurry is applied proximal to the corneal limbus.

In some embodiments, the prolonged hypesthesia lasts more than about 1 day following a single treatment of the topical application of the cold slurry.

In some embodiments, the ocular sensation of the eye is restored by about 30 days following the topical application of the cold slurry.

In some embodiments, the cold slurry is topically applied for between about 5 minutes and about 15 minutes.

In some embodiments, the method further comprises placing a contact lens on the eye of the patient prior to topically applying the cold slurry, and wherein the contact lens prevents the cornea of the eye from freezing.

BRIEF DESCRIPTION OF THE DRAWINGS

The following figures depict illustrative embodiments of the invention.

FIG. 2 is a table showing the breakdown by volume and weight of components of an exemplary biomaterial that can form an injectable cold slurry.

FIG. 7 is a graph showing hypesthesia in rabbits' eyes over time following administration to the eye, with the cornea not exposed, of a topically applied cold slurry.

DETAILED DESCRIPTION

Figure 1:
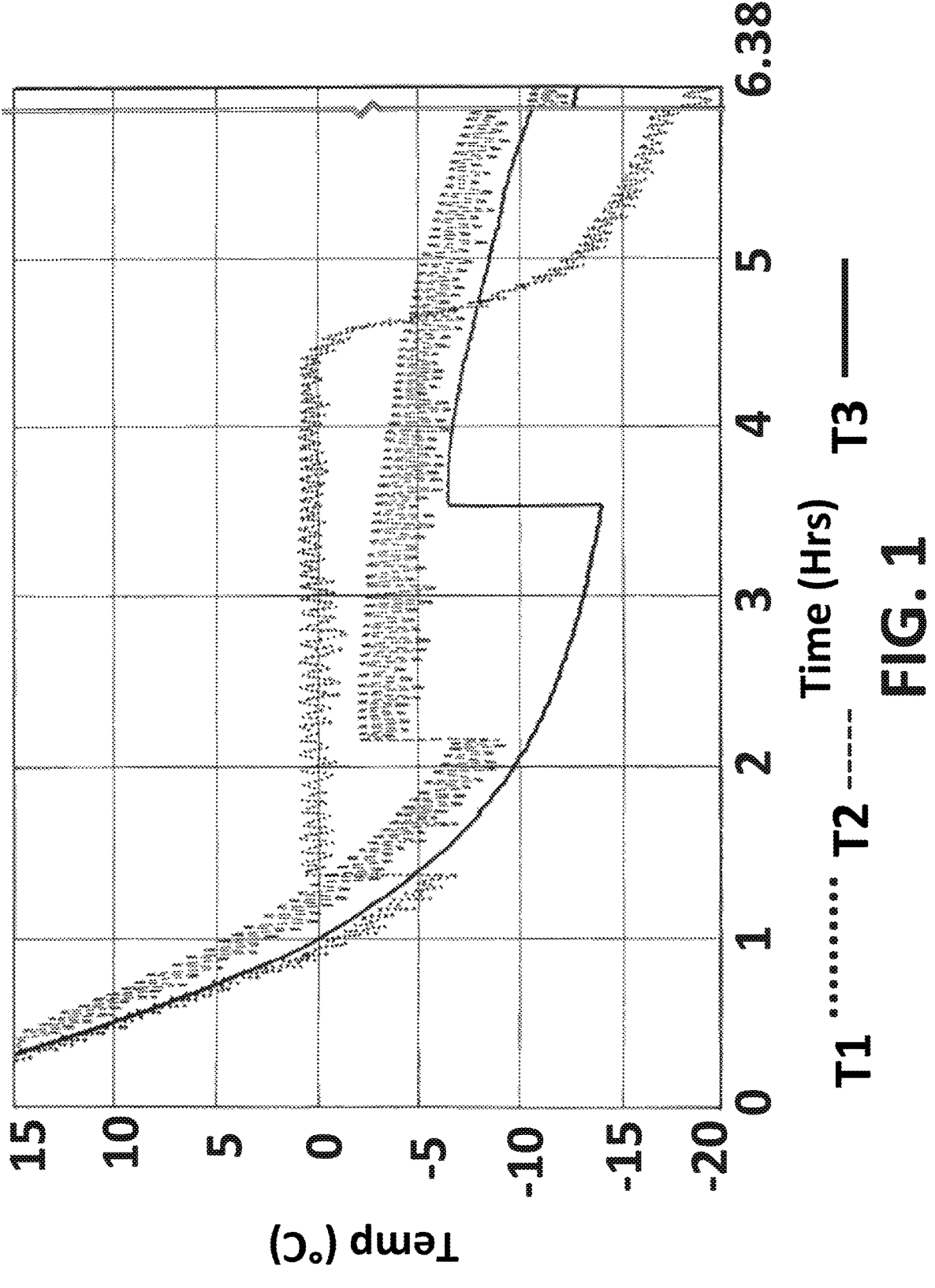
FIG. 1 depicts a freezing point depression graph for liquid water, a solution containing 10% glycerin volume by volume (v/v), and a solution containing 20% glycerin (v/v).

The present disclosure is drawn to apparatuses, devices, systems, and methods of treating ocular surface discomfort with a biological material, such as a cold slurry. In some embodiments, the biomaterial is a cold slurry (e.g., ice slurry) that can be delivered via topical application or via injection into the eye of a human patient or a subject (e.g., a human who is not a patient or a non-human animal) for prophylactic or therapeutic purposes to reduce ocular discomfort. The systems and methods disclosed herein provide for a hypesthesia of the eye that is unexpectedly long-lasting. The hypesthesia may cause a long-lasting corneal numbing followed by a restoration of ocular sensation within days or weeks following application of cold slurry treatment, without causing permanent damage to the cornea or disrupting the progress of corneal healing.

In some embodiments, the cold slurry can be applied topically to achieve a desired therapeutic effect such as amelioration or treatment of ocular surface discomfort through long-term corneal numbing. In some embodiments, the therapeutically effective cold slurry is comprised entirely of water and excipient materials (i.e., materials without an active pharmaceutical compound). In other embodiments, the cold slurry further comprises a known active pharmaceutical compound. In some embodiments, a layer of protection, like a contact lens, is applied to the cornea prior to the topical application of the slurry. In some embodiments, the eyelid is protected from topical application of the slurry by inserting a plastic, or other non-thermally conductive material, speculum into a subject's eye.

In some embodiments the length of time that the slurry is applied to a subject's eye can be varied to induce a greater or milder hypesthesia. In some embodiments, the temperature of the slurry applied or injected into a subject's eye is varied to induce a greater or milder hypesthesia. In some embodiments, the hypesthesia decreases over time to the point where it is not noticeable. In other embodiments, where a subject's eye may be particularly sensitive, a greater hypesthesia is induced to numb more of the nerves in the subject's eye.

In some embodiments, a container (e.g., vial, syringe) containing a biomaterial is received at a clinical point of care. The biomaterial may be received in a crystallized (or partially crystallized) state. In some embodiments, the final product to be administered via topical application or injection to a human patient or a subject (such as a human who is not a patient or a non-human animal) is a cold slurry comprised of sterile ice particles of water and varying amounts of excipients or additives such as freezing point depressants. For example, the percentage of ice particles in the cold slurry can constitute less than about 10% by weight of the slurry, between about 10% by weight and about 20% by weight, between about 20% by weight and about 30% by weight, between about 30% by weight and about 40% by weight, between about 40% by weight and about 60% by weight, more than about 60% by weight, and the like. The sizes of the ice particles will be controlled to allow for flowability through a vessel of various sizes (e.g. needle gauge size of between about 7 and about 43) as described in U.S. application Ser. No. 15/505,042 (Publication No. US2017/0274011) and incorporated herein by reference. Further, other methods may be used to condition the size of the ice particles to allow for flowability through a vessel of various sizes. In some embodiments, the majority of ice particles have a diameter that is less than about half of the internal diameter of the lumen or vessel used for injection. For example, ice particles can be about 1.5 mm or less in diameter for use with a 3 mm catheter.

There are a variety of techniques that may be used to prepare a cold slurry. This disclosure is not limited to any particular method or technique.

In some embodiments, one or more excipients may be included in the cold slurry. An excipient is any substance, not itself a therapeutic agent, used as a diluent, adjuvant, and/or vehicle for delivery of a therapeutic agent to a subject or patient, and/or a substance added to a composition to improve its handling, stability, or storage properties. Excipients can constitute less than about 10% volume by volume (v/v) of the cold slurry, between about 10% v/v and about 20% v/v of the slurry, between about 20% v/v and about 30% v/v, between about 30% v/v and 40% v/v, and greater than about 40% v/v. Various added excipients can be used to alter the phase change temperature of the cold slurry (e.g., reduce the freezing point), alter the ice percentage of the cold slurry, alter the viscosity of the cold slurry, prevent agglomeration of the ice particles, prevent dendritic ice formation (i.e., crystals with multi-branching "tree-like" formations, such as those seen in snowflakes), keep ice particles separated, increase thermal conductivity of fluid phase, or improve the overall prophylactic, therapeutic, or aesthetic efficacy of the cold slurry.

One or more freezing point depressants can be added as excipients to form cold slurries with freezing points below 0° C. Depressing the freezing point of the slurry allows it to maintain flowability and remain injectable while still containing an effective percentage of ice particles. Suitable freezing point depressants include salts (e.g., sodium chloride, betadex sulfobutyl ether sodium), ions, Lactated Ringer's solution, sugars (e.g., glucose, sorbitol, mannitol, hetastarch, sucrose, (2-Hydroxypropyl)-β-cyclodextrin, or a combination thereof), biocompatible surfactants such as glycerol (also known as glycerin or glycerine), other polyols (e.g., polyvinyl alcohol, polyethylene glycol 300, polyethylene glycol 400, propylene glycol), other sugar alcohols, or urea, and the like. Other exemplary freezing point depressants are disclosed in U.S. application Ser. No. 15/505,042 (Publication No. US2017/0274011) and are incorporated in their entirety herein. In other embodiments, a slurry paste is formed that has the consistency of toothpaste and has a consistency that is optimal for topical application.

The concentrations of freezing point depressants will determine the ice particle percentage of the cold slurry and its flowability and injectability. The degree of freezing point depression can be calculated using the following formula as described in U.S. application Ser. No. 15/505,042 (Publication No. US2017/0274011), incorporated herein:

$$\Delta T_F = K_F bi$$

wherein $\Delta T_F$ is the freezing point depression (as defined by $T_{F\ (pure\ solvent)} - T_{F\ (solution)}$), $K_F$ is the cryoscopic constant, b is molality, and i is the van't Hoff factor representing the number of ion particles per individual molecule of solute. Other methods of computing freezing point depression can also be used, as disclosed in U.S. application Ser. No. 15/505,042 (Publication No. US2017/0274011).

Referring to FIG. 1, a freezing point depression graph is shown for pure water T1, a mixture of water and 10% (v/v) glycerin T2, and a mixture of water and 20% (v/v) glycerin T3. In this graph, all the substances were placed in a freezer having a constant temperature of −20° C. The temperature was measured using a thermometer placed in each substance. The graph shows that a mixture of water and glycerin will have a different freezing point than that of pure water, which means the solution can be cooled to below 0° C. and only be partially crystallized. The graph shows that cooling causes pure water T1 to crystallize at an equilibrium freezing point of 0° C. This is indicated by the period of time where the pure water remains at a temperature of about 0° C., from about 1.3 hours to about 4.4 hours, which begins immediately after pure water T1 passes a supercooling point at about −6° C. Having an equilibrium window of crystallization (i.e., the "flat line" portion of pure water T1 in FIG. 1) is typical for a pure solvent. For the 10% glycerin solution T2, cooling causes the solution to begin crystallizing at an initial freezing point of about −3° C. after about 2.2 hours, and the crystallization continues as the temperature of the solution drops further to about −8° C. after about 6 hours. The initial crystallization occurs immediately after 10% glycerin solution T2 passes a supercooling point at about −8° C. (which can vary from sample to sample, e.g., supercooling point of between about −15° C. and about −3° C.), shown at around 2.2 hours. Having a descending temperature window of crystallization for the 10% glycerin solution T2 is typical for a solution (i.e., impure mixture). Similarly, for the 20% glycerin solution T3, cooling causes the solution to begin crystallizing at an initial freezing point of about −7° C. after about 3.5 hours (following an initial supercooling point which can vary from sample to sample, e.g., between about −25° C. and about −5° C.), and the crystallization continues as the temperature of the solution drops further to about −11° C. after about 6 hours and continues to decline thereafter past 6.5 hours. The initial crystallization occurs immediately after 20% glycerin solution T3 passes a supercooling point at about −14° C., shown at around 3.5 hours. Similar to the trace for 10% glycerin solution T2, the descending temperature window of crystallization for 20% glycerin solution T3 is typical for a solution.

Referring to FIG. 2, this chart shows the components of an exemplary biomaterial that can form a cold slurry. This chart shows that the percentage of ice for an exemplary biomaterial can be calculated for a particular temperature. The exemplary slurry contains 30% ice by mass (weight by weight; w/w) at −10° C. This exemplary slurry has 80 mL of saline (0.9% NaCl) and 20 mL of glycerol (i.e., glycerin). In weight, such a slurry has about 79.6 g of pure water, about 0.72 g of sodium chloride, and about 25.2 g of glycerol (approximately 20% v/v). In other embodiments, the slurry could contain higher or lower percentages of glycerol by adjusting the relative volume of glycerol to saline. For example, other suitable slurries contain about 10% glycerol (v/v), between about 10% and about 20% glycerol, about 30% glycerol, or more than about 30% glycerol. If an active pharmaceutical compound is to be added to the slurry, the concentration of saline can be adjusted accordingly to maintain the desired concentration of excipients such as glycerol. The percentage of ice will vary depending on the composition of the biomaterial.

Figure 3:
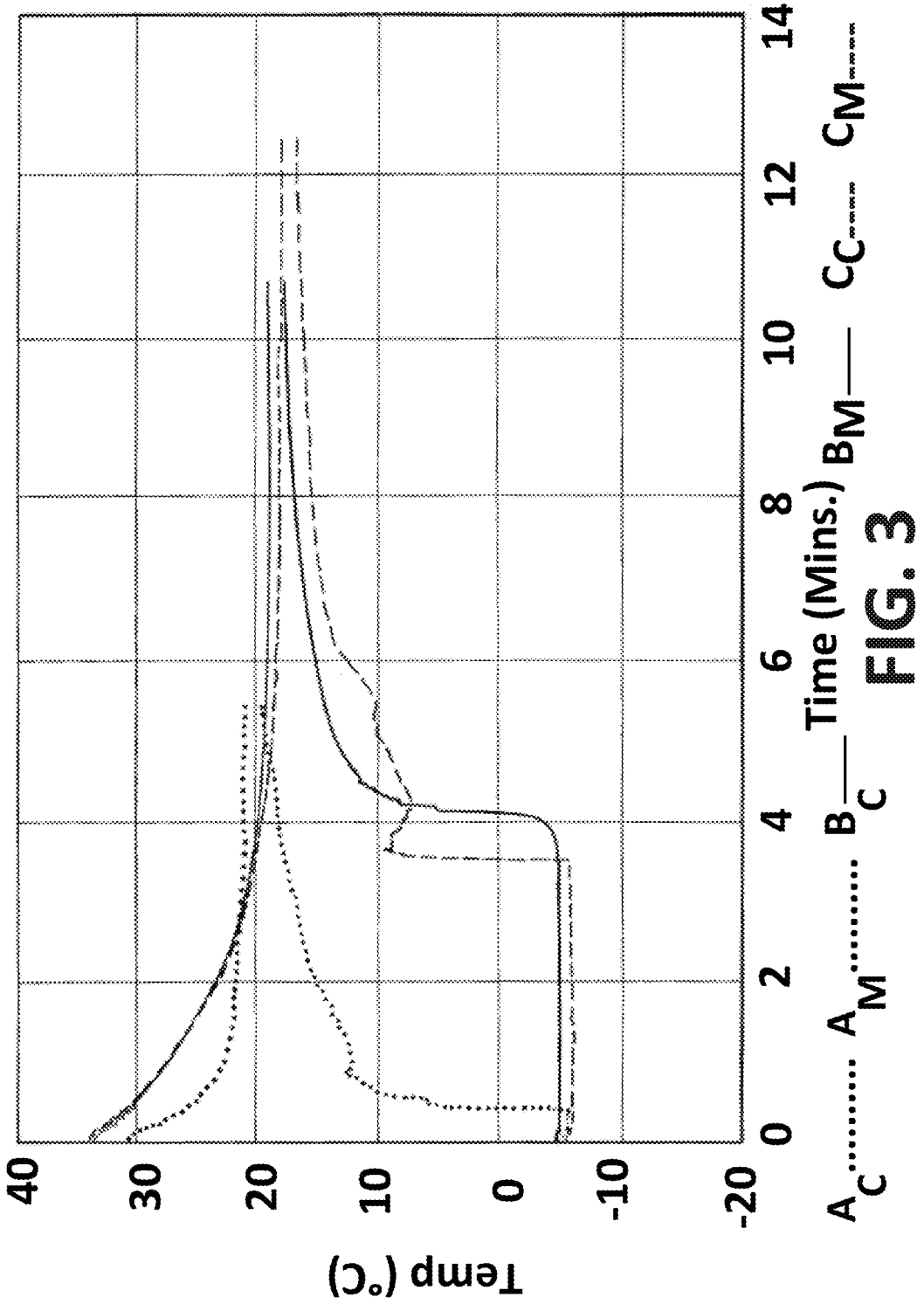
FIG. 3 is a graph showing the characterization of ice content of cold slurries having crystallization set points of –5.5° C. and –8.1° C.

Referring to FIG. 3, different slurry compositions (batches) are characterized with respect to their temperature profiles and ice content. The different slurry batches were placed into a copper plate that is heated to 40° C. and has thermocouple wires that measure changes in temperature of the slurry over time. The plotted data shows temperature change over time for three different slurry batches. The temperatures are measured at two different positions for each slurry: embedded inside of the copper plate (traces $A_C$, $B_C$, and $C_C$) and in the middle of the copper plate exposed to the outside of the plate (traces $A_M$, $B_M$, and $C_M$). The temperature traces show three separately created slurry batches: a slurry composition having 15% glycerin (having a temperature setpoint of −8.1° C.) is represented by traces $A_C$ and $A_M$, and two different slurry batches both having 10% glycerin (having a temperature setpoint of −5.5° C.) are represented by traces $B_C$ and $B_M$, as well as traces $C_C$ and $C_M$. When a slurry batch is first introduced into the copper plate, the thermocouple wire embedded inside the plate (traces $A_C$, $B_C$, and $C_C$) initially measures the warm temperature of the heated plate (e.g., 31° C. for trace $A_C$ at timepoint 0) and then reaches an equilibrium at a lower temperature due to the cooling effect of the introduced slurry (e.g., 22° C. for trace $A_C$ at around 2 minutes). On the other hand, for the thermocouple wire located in the middle of the plate, when a slurry is first introduced into the copper plate it immediately contacts the thermocouple wire since that wire is exposed. This causes an initially negative temperature reading in the middle position due to the crystallized slurry contacting the wire (e.g., −5° C. for trace $A_M$ at timepoint 0) followed by an equilibrium at a warmer temperature as the slurry begins to melt on the heated plate (e.g., 18° C. for trace $A_M$ at around 4 minutes). The thermocouple wire exposed to the outside of the plate (traces $A_M$, $B_M$, and $C_M$) can be used to detect phase transitions during which the crystallized slurry begins to melt. The graph shows that the two slurry compositions with 10% glycerin reach their phase transition at similar timepoints (at around 4 minutes for trace $B_M$, and at around 2.7 minutes for trace $C_M$), which differ from the phase transition for the 15% glycerin slurry (phase transition occurs at around 0.2 minutes for trace $A_M$). The graph also shows that the two slurry batches having the same composition (10% glycerin: traces $B_C$ and $B_M$ and traces $C_C$ and $C_M$) reach equilibrium (as measured by the two thermocouple wire positions) in a similar time frame and at similar temperatures of between about 15° C. and 19° C. depending on the location of the thermocouple (middle/bottom). On the other hand, the slurry with a different composition (15% glycerin: traces $A_C$ and $A_M$) has a different temperature profile from the other two, reaching an equilibrium sooner at the temperature of between about 19° C. and 22° C. depending on the location of the thermocouple (middle/bottom). FIG. 3 therefore demonstrates that slurries of different compositions have different temperature profiles and batch to batch consistency exists across slurries having the same composition (e.g., the slurry represented by $B_C$ and $B_M$ and slurry represented by $C_C$ and $C_M$ have similar temperature profiles which is different from that of slurry represented by $A_C$ and $A_M$).

Figure 4A:
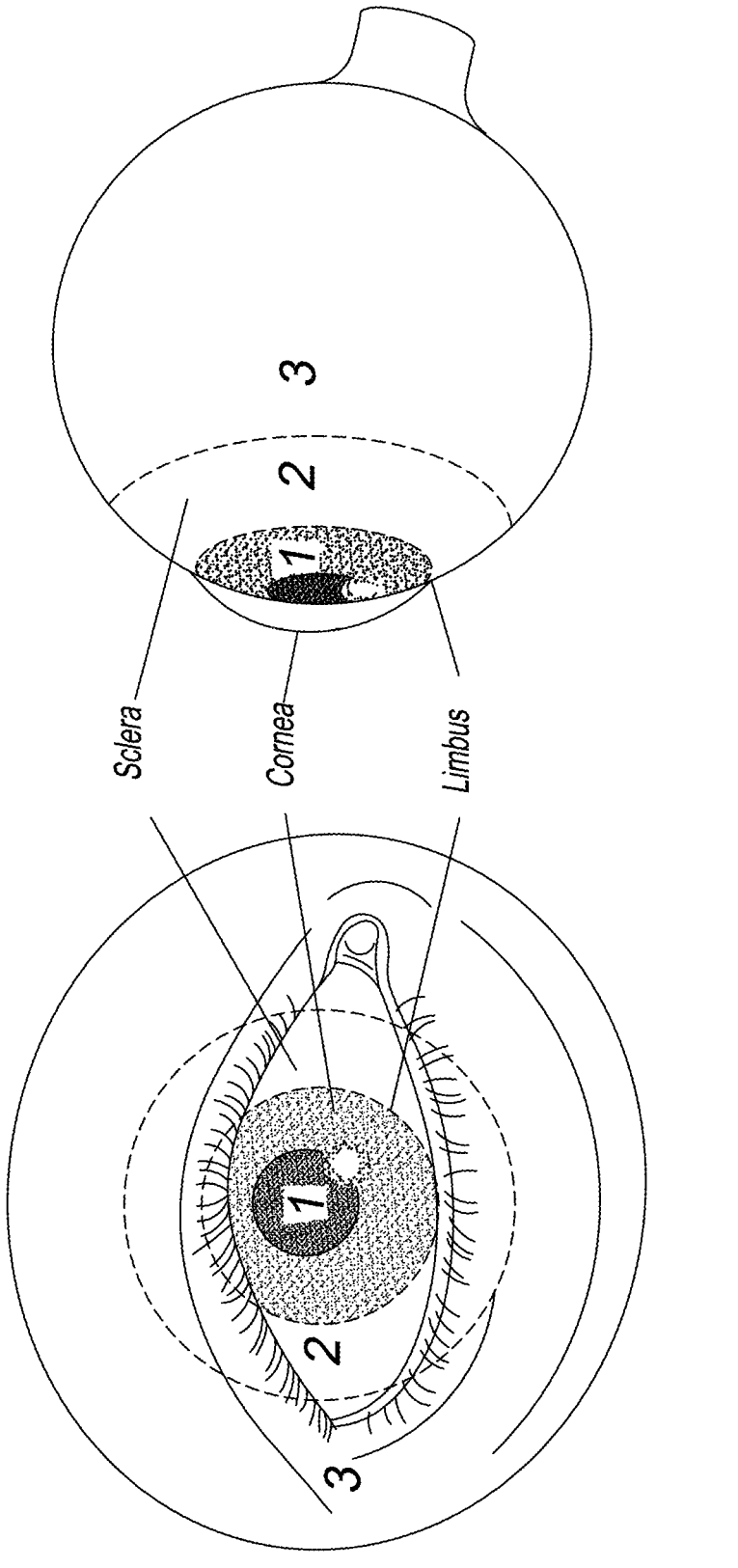
FIGS. 4A and 4B show diagrams of a human eye showing different areas of the eye (FIG. 4A) and degrees for anatomical reference (FIG. 4B).
Figure 4B:
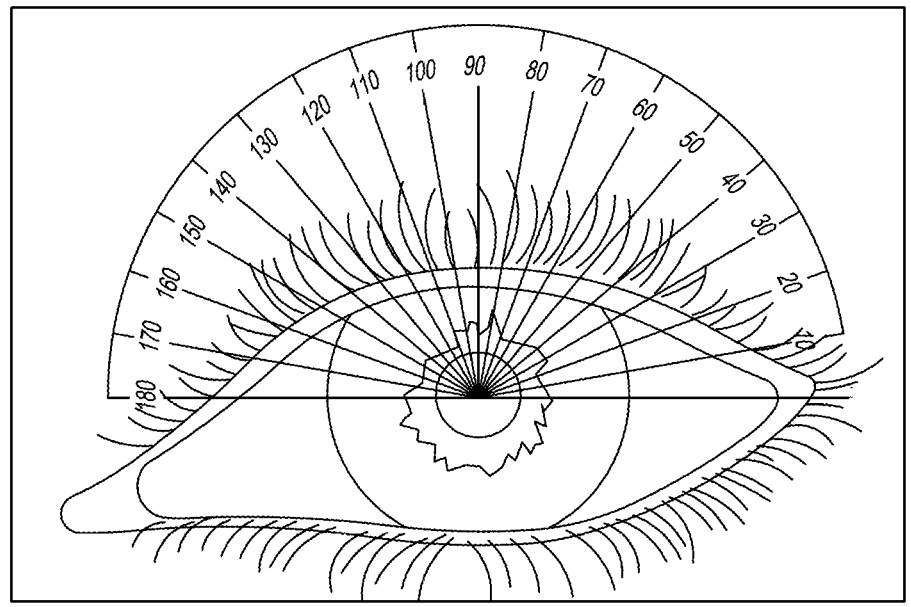

With reference to FIG. 4A, a diagram of an eye is shown depicting the sclera zone 2, sclera zone 3, cornea 1, and the corneal limbus (dotted line between cornea 1 and sclera zone 2. FIG. 4A is reproduced from Andreoli C M, Gardiner M F. Open globe injuries: Emergent evaluation and initial management. In: UpToDate, Post TW (Ed), UpToDate, Waltham, MA. FIG. 4B shows a diagram of an eye with a superimposed protractor showing angles in degrees (°) with respect to the eye. In this diagram, 90° represents the superior most position along the eye.

In some embodiments, the cold slurries described herein can be applied topically, or alternatively injected, to achieve long-lasting hypesthesia that reduces ocular surface discomfort. Hypesthesia refers to a reduction of ocular discomfort or pain without a complete blockage of ocular sensation. Hypesthesia is therefore distinguished from anesthesia, anesthesia being characterized as a more profound blockage of ocular sensation. Hypesthesia may include corneal numbing which causes a reduction in pain response, while maintaining an otherwise normal functioning of the eye, including a normal healing process. Anesthesia, on the other hand, may lead to abnormal functioning of the eye since all corneal sensation is lost. Corneal sensation is important for normal functioning of the eye including the initiation of protective mechanisms such as blinking and tear production.

One approach is to apply drops of the cold slurry to the ocular surface which may vary in volume from 1 to 100 microliters, preferably from approximately 10 to 80 microliters. As drops, the formulation may be directly administered to the ocular surface. Alternatively, the cornea may be scraped first, and drops may be subsequently administered. In some embodiments, the topically applied cold slurry has a more flowable paste consistency, and a large quantity, could be applied topically (3-50 ml) to the ocular surface as a treatment.

In some embodiments, the cold slurries as described herein are applied topically posterior to the corneal limbus, e.g., the area denoted as sclera zone 2 in FIG. 4A, for between about 1 minute and about 20 minutes. In some embodiments, the cold slurry is applied for between about 5 minutes and about 10 minutes. In some embodiments, cold slurry is administered every 1 to 10 seconds for 1 to 20 minutes into each eye. This treatment could be repeated several times over a short period of time (e.g., 5-20 min). In some embodiments, the cold slurry is applied topically posterior to the corneal limbus for about 10 minutes, with fresh slurry re-applied every 90 seconds until 10 minutes is reached.

In some embodiments, during the topical application, sensitive ocular structures are protected from encountering the cold slurry in order to limit potential side effects. Protection of the corneal surface may limit some or all corneal cell damage or refractive changes caused by freezing the corneal tissue. Protection of the palpebral conjunctiva and eye lids may prevent redness, swelling and inflammation that would not be related to the treatment effect. By selectively applying ice to the ocular surface posterior to the limbus over the bulbar conjunctiva (Corresponding to the anterior anatomical area known as zone 2, FIG. 4A), potential adverse effects to the cornea may be minimized.

In some embodiments, a protective contact lens or other protective cover can be applied to sit on the cornea to protect the cornea from damage. In some embodiments, a corneal covering completely blocks the cold slurry from contacting the cornea surface directly. In some embodiments, a lid speculum is used to keep the eye lids open during cold slurry topical application. In some embodiments, the speculum is made of a thermally non-conductive material such as plastic or another other non-conductive material known in the art. A thermally non-conductive material may be used for the speculum to prevent the eyelids (inside and outside) from freezing, which could cause damage to the eyelids, during cold slurry treatment. In some embodiments, the cold slurry is applied to the sclera only and the cornea is protected from freezing. In some embodiments, preventing the cornea from freezing will ensure faster healing of the cornea.

Figure 10:
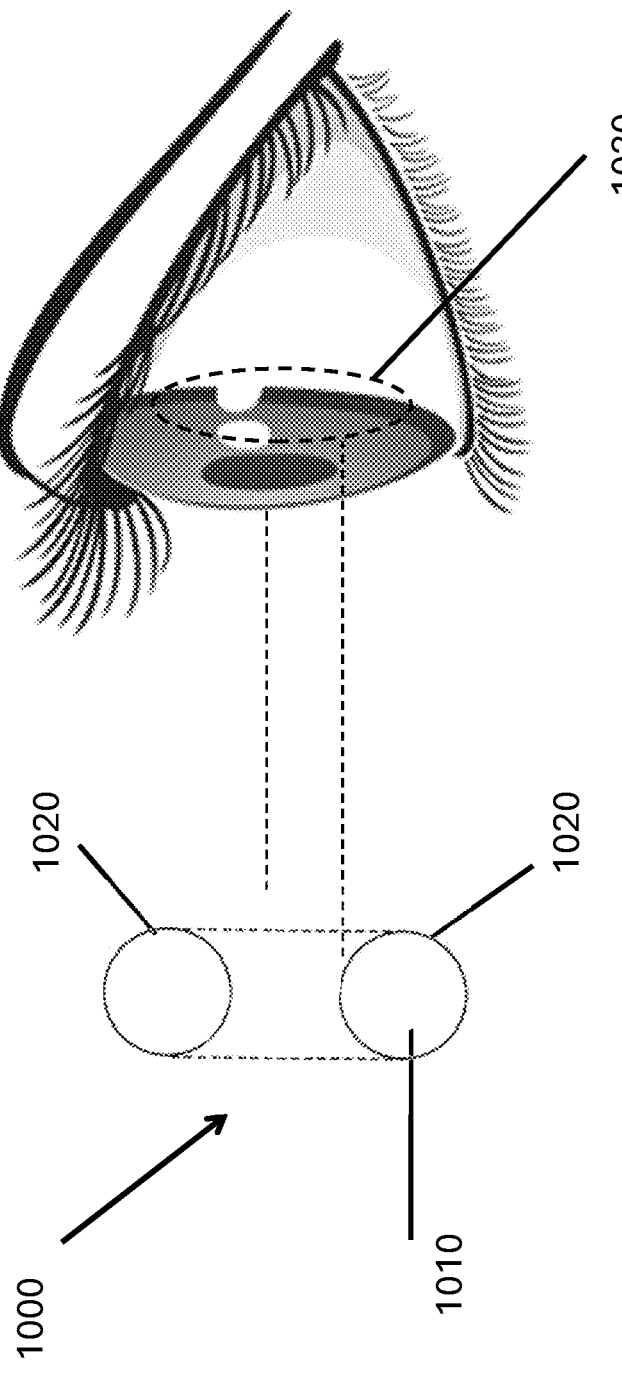
FIG. 10 depicts a device for cooling one or more areas of therapeutic effect of an eye, according to some embodiments of the present disclosure.

As shown in FIG. 10, according to some embodiments, a device 1000 could be used to control the areas exposed to the cold slurry to just the bulbar conjunctiva/sclera so that the cold slurry could not physically contact or freeze adjacent tissues that would not relevant to the desired clinical effect. In some embodiments, the cold slurry formulation does not have direct contact with the ocular surface at all. The cold slurry formulation may be contained within a material (e.g. container 1010) that is thermally conductive, e.g., a small metal or polymeric donut or other protective ring, thus providing a barrier (e.g. barrier 1020) against direct contact of the formulation with the ocular surface but allowing the requisite cooling to occur. In some embodiments, the device directs cooling only to the areas of potential therapeutic effect (e.g. areas 1030) and prevents the device/cooling from contacting and affecting adjacent tissues in order to minimize undesired side effects (e.g., potential irritation of the eye from the application of a hyperosmolar solution directly to the eye).

In some embodiments, the cold slurries described herein are injected as a subconjunctival bolus, at about every 2 minutes. Each injection could provide approximately 0.5-1.5 ml of frozen slurry and be repeated every approximately 2 minutes for the duration of desired treatment, or about 10 minutes in total. In some embodiments, the cold slurry is injected more directly near the axons of the ciliary nerves. The ciliary nerves are located at approximately 0° and 180° of the eye (FIG. 4B).

In some embodiments, a standard syringe is used to inject slurry. Alternatively, a syringe that has conditioned the slurry for injection may be used. In some embodiments, the syringe may have a needle of about 18G to about 25G.

In some embodiments, real-time temperature sensing on the surface of the eye is performed during the treatment (e.g., cold slurry injection or topical application). In some embodiments, the cold slurry is applied to cool the tissue (e.g., corneal surface, conjunctiva, or any other part of the eye) to less than about 0° C., less than about −1° C., less than about −2° C., less than about −3° C., less than about −4° C., or less than about −5° C. In some embodiments, the cold slurry is applied for over about one minute, preferably for between about 2 minutes and about 10 minutes. The temperature of the cooled tissue and the length of time that the slurry is applied can be varied to vary the hypesthesia experienced by a subject.

In some embodiments, the cold slurry is periodically readministered to a subject's eye over time to maintain therapeutic effects. There is a range of possible frequencies for topical administration and/or injection. For example, treatment could be administered any one of the following: once every other week; once a month; once every other month; once every third month, etc.

In some embodiments, cold slurry is used as a safe corneal numbing treatment to treat corneal discomfort or pain. Various formulations of cold slurries can be used with the methods described herein, including those described above. Additional specific embodiments of cold slurries are described with reference to FIGS. 5-9. "ECT-4143" is a slurry formulation that comprises 15% glycerol, 30% L-α-phosphatidylcholine liposomes, and 0.9% saline (or phosphate buffered saline). In some embodiments, ECT-4143 is administered to the eye (topically or via injection) at a temperature of between about −25° C. and −10° C. (temperature of the slurry). In some embodiments, ECT-4143 is administered to the eye (topically or via injection) at a temperature of about −18° C. (temperature of the slurry, such as in the embodiments described below with reference to FIGS. 5-9). ECT-4143 is administered every approximately 90 seconds, with approximately 2-3 ml per application, until a total treatment time of 10 minutes is reached.

"ECT-1719" is a slurry formulation that comprises 15% glycerol and 0.9% saline (or phosphate buffered saline). In some embodiments, ECT-1719 is administered to the eye (topically or via injection) at a temperature of between about −20° C. and −5° C., or between about −15° C. and about −10° C. (temperature of the slurry). In some embodiments, ECT-1719 is administered to the eye (topically or via injection) at a temperature of about −11° C. (temperature of the slurry, such as in the embodiments described below with reference to FIGS. 5-9). In some embodiments, ECT-1719 is injected in 0.7 ml volume per injection, with four total injections making up 2.8 ml total injected volume. ECT-1719 is administered every approximately 120 seconds until a total treatment of 10 minutes is reached.

Figure 5:
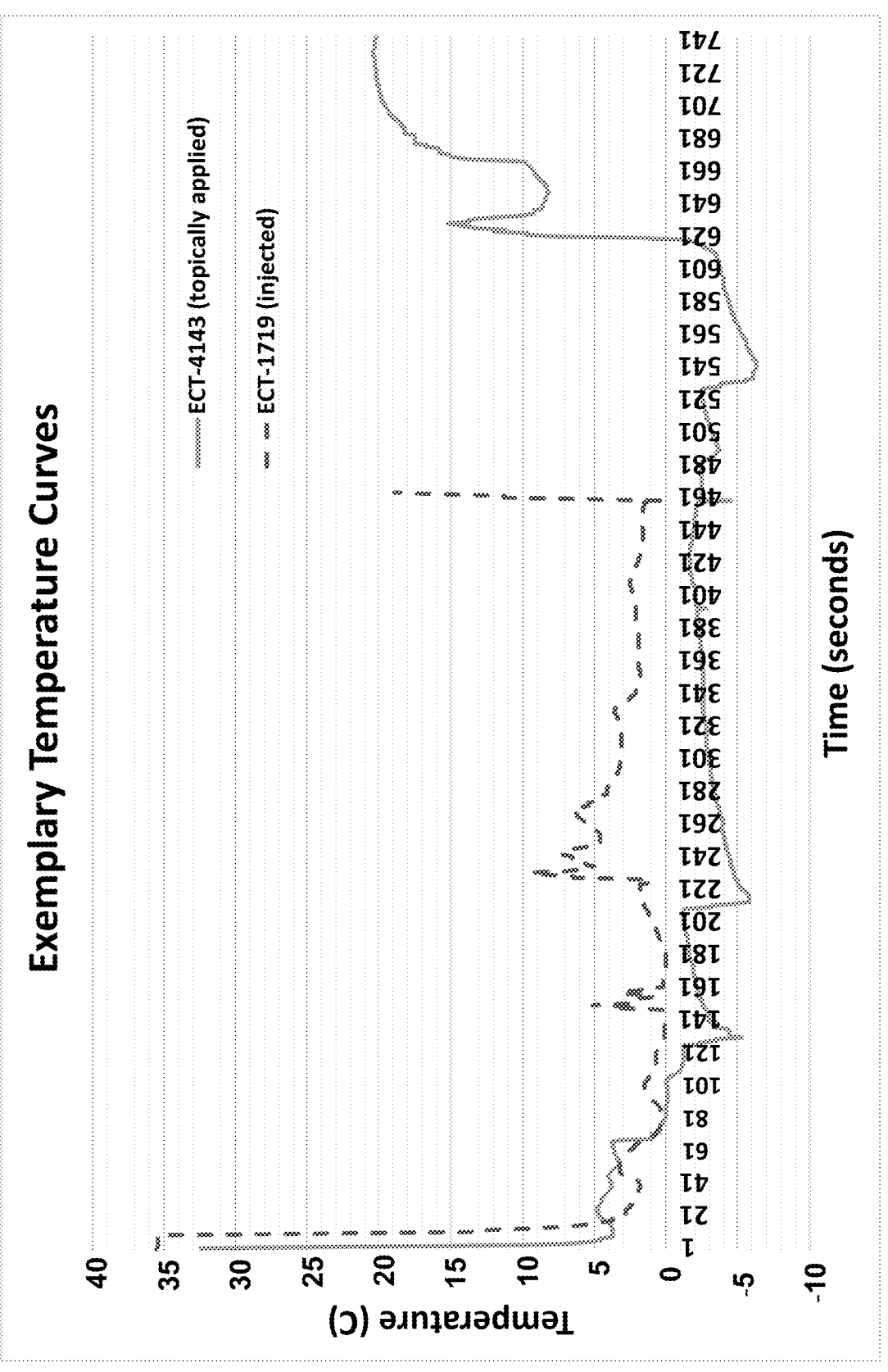
FIG. 5 is a graph showing real-time scleral temperature monitoring in rabbits following administration to the eye of a topically applied cold slurry (solid line) and an injected cold slurry (dashed line).

Referring to FIG. 5, real-time scleral temperature monitoring was performed in rabbits following administration to the eye of a topically applied cold slurry (ECT-4143, solid line) in one rabbit and an injected cold slurry (ECT-1719, dashed line) in a second rabbit. The temperature monitoring is achieved by cannulating the subtenon's space with a 25 g needle containing a temperature probe at its distal end. As can be seen in FIG. 5, the scleral temperature of the rabbit that received the injected cold slurry (ECT-1719) fluctuated between about 0° C. and about 8° C. throughout the duration of the procedure (from about 0 seconds following cold slurry injection to about 463 seconds following cold slurry injection). The sharp line in the graph at about 463 seconds represents conclusion of the study after 7.5 minutes and removal of the temperature probe from the ocular tissue. The scleral temperature of the rabbit that received the topically applied cold slurry (ECT-4143) was lower than for the injected cold slurry with fluctuations between about −6° C. and about 4° C. for the majority of the time during which temperature was recoded (between about 0 seconds following topical application and about 600 seconds following topical application). Following topical application, the temperature of the sclera continued to drop from about 4° C. at the time of application (about 0 seconds in FIG. 5) to about 0° C. after about 120 seconds. Following the initial period of scleral cooling, the temperature remained relatively stable at between about 0° C. and −5° C. from about 120 seconds after topical application to about 520 seconds after topical application. Additionally, for a duration of between about 220 seconds and about 520 seconds following topical application, the scleral temperature showed very little variability, remaining stable at about −2° C. to about −3° C. After about 620 seconds following topical application, the treatment is concluded and the temperature probe is removed, showing a sharp increase in measured temperature as shown in FIG. 5.

The hypesthetic effect following cold slurry treatment is measured as a response to tactile stimulation of the eye using a monofilament/esthesiometer. Starting at 6 cm filament length and decreasing by 0.5 cm increments, the eye is probed three times at each length until a blink response is elicited. The filament gets stiffer as it is shortened, therefore imparting more pressure on the eye when probed into the eye. The hypesthesia for each time point is based on a given length of the monofilament. At each time point, the specific monofilament length that is recorded is the shortest length (highest pressure) at which blink response is not present. For example, starting with the longest monofilament of 6 cm, if the rabbit does not blink when probed, the next monofilament of 5.5 cm length is used to probe the eye. If the rabbit does not blink again, the next monofilament length of 5 cm is used. Now, if the rabbit does blink, the previous length of 5.5 cm is recorded because this is the shortest length at which there was no blink response (reflecting a certain degree of hypesthesia). The deepest level of hypesthesia is when a rabbit does not blink when probed with the shortest filament length (e.g., 0.5 cm). Zero degree of hypesthesia (no blockage of pain/no numbing) is when a rabbit blinks when probed with the longest filament length (e.g., 6 cm). The filament length can be converted into a pressure (g/mm$^2$) such that 6 cm filament produces 0.4 g/mm$^2$ pressure (the lowest pressure), while 0.5 cm filament produces 15.9 g/mm$^2$ pressure (the highest pressure). Therefore, the recorded pressure is the pressure that corresponds to the shortest filament length where blink response is not present.

Figure 6:
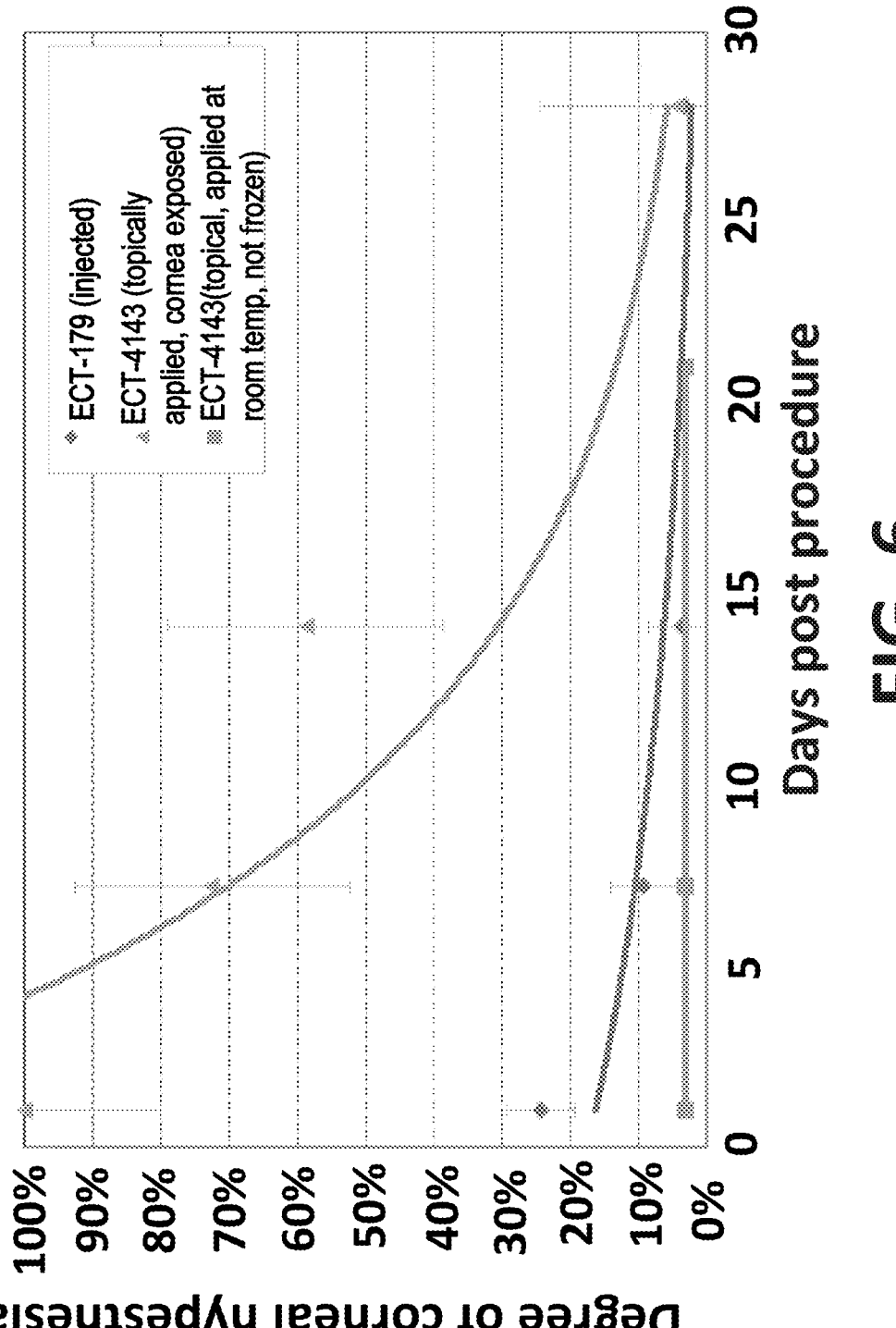
FIG. 6 is a graph showing hypesthesia in rabbits' eyes over time following administration to the eye, with the cornea exposed, of an injected cold slurry (diamond), a topically applied cold slurry (triangle), and a topically applied slurry at room temperature (square).

Referring to FIG. 6, the hypesthetic effect (degree of corneal numbing measured using tactile stimulation as described herein) was measured in rabbits over time following administration to the eye, with the cornea exposed, of an injected cold slurry (ECT-1719, 3 rabbits in this group, shown with a diamond), a topically applied cold slurry (ECT-4143, 3 rabbits in this group, shown with a triangle), and a topically applied slurry at room temperature (ECT-4143, 1 rabbit in this group, shown with a square). In FIG. 6, the degree of hypesthesia is shown as a percentage of the recorded pressure (i.e., based on the shortest monofilament in which there is a lack of blink response) relative to the highest possible pressure (i.e., shortest monofilament used of 0.5 cm corresponding to 15.9 g/mm$^2$ pressure). The degree of hypesthesia is shown for days 1, 7, 14, and 28 following cold slurry administration. For the injected cold slurry (ECT-1719, shown with a diamond), the hypesthetic effect at day 1 was about 20% and continued to taper off reaching baseline levels by day 14 (error bar overlaps with 0%). For the topically applied cold slurry (ECT-4143 applied at 18° C., shown with a triangle), the hypesthetic effect at day 1 was 100% (maximal corneal numbing that could be measured), which then continued to drop, tapering off at day 28 during which the pain response returned to baseline levels (error bar overlaps with 0%). For the topically applied slurry at room temperature (ECT-4143, shown with a square), no hypesthetic effect could be observed at any time point following treatment. FIG. 6 therefore demonstrates an unexpectedly strong hypesthetic effect for topically applied cold slurry which results in long-lasting hypesthesia (almost 1 month). Injected cold slurry results in moderate hypesthesia which also lasted longer than expected (e.g., between about 1 week and 2 weeks). Importantly, for both topical and injection methods, cold slurry treatment produced long-lasting hypesthesia which normalized back to baseline levels without causing any permanent numbing effect.

FIG. 7 shows hypesthetic effect in rabbits over time following administration to the eye of a topically applied cold slurry (6 rabbits, ECT-4143) similar to FIG. 6, except with the cornea not exposed (protected with a contact lens).

The hypesthetic effect was measured in the same way as described above with respect to FIG. 6. The hypesthetic effect is shown for days 1, 7, 14, 21, and 28 following treatment with the topically applied cold slurry. The hypesthetic effect was at about 50% at day 1 and tapered off slowly reaching baseline levels by day 21 (error bar overlaps with 0%). FIG. 7 therefore demonstrates an unexpectedly moderate-to-strong hypesthetic effect for topically applied cold slurry (with corneal protection) which results in long-lasting hypesthesia (about 3 weeks) without causing permanent corneal numbing or any corneal damage.

Figures 8A, 8B:
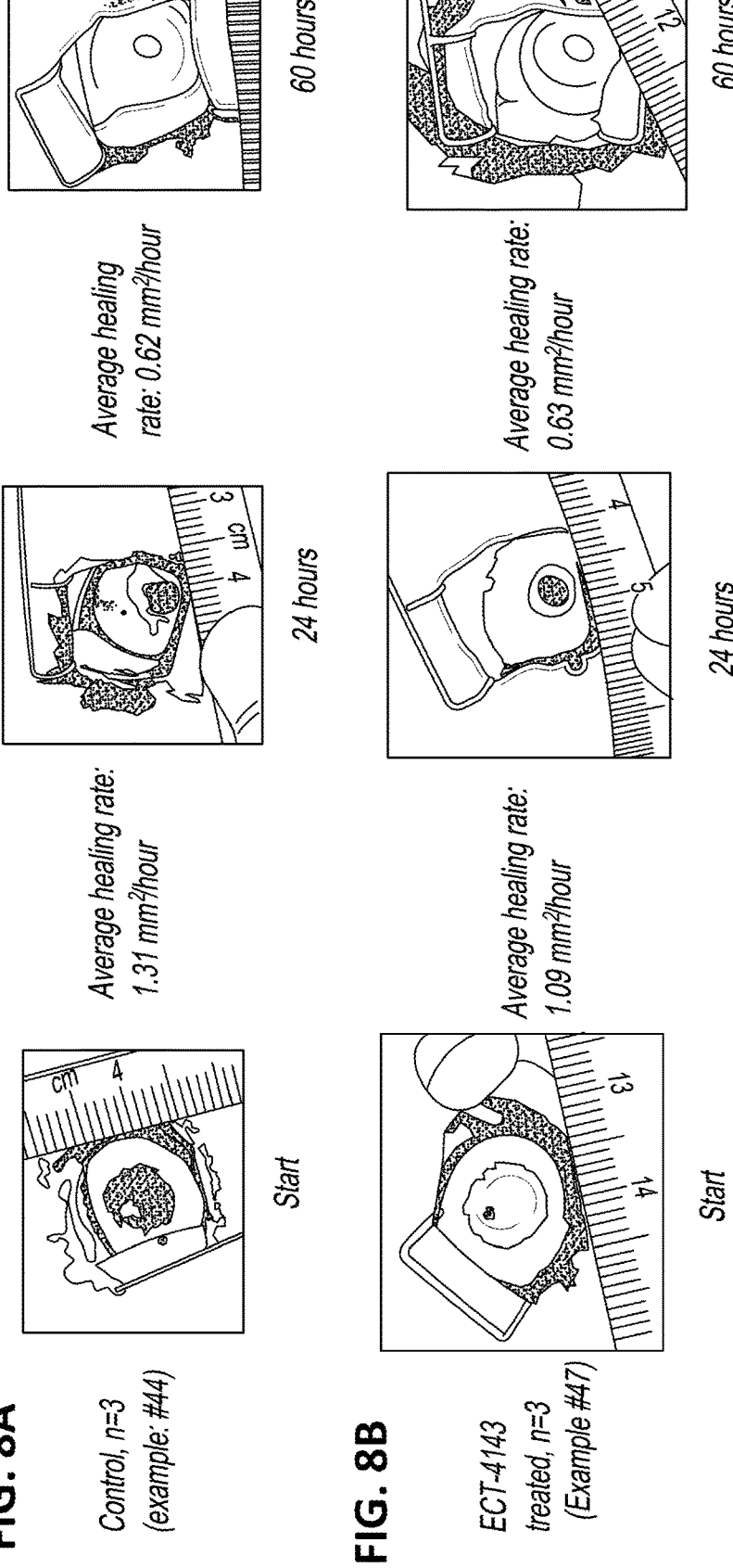
FIGS. 8A and 8B are images of fluorescein stained rabbit cornea showing corneal healing over time following intentional 8 mm corneal abrasion (FIG. 8A) as a control group and following topical application of cold slurry (FIG. 8B).

Referring to FIG. 8, representative images of rabbit corneas using fluorescein staining demonstrate corneal healing over time following intentional 8 mm corneal abrasion applied to both the control group (FIG. 8A) and following topical application of cold slurry in the treatment group (FIG. 8B) with protection applied to the corneas and eyelids. The progress of the injury is determined by measuring the size of the injury over time. As can be seen in FIG. 8A, corneal healing in the control group (3 rabbits) occurred at an average healing rate of 1.31 $mm^2$/hour in the first 24 hours following corneal abrasion and 0.62 $mm^2$/hour between 24 hours and 60 hours following corneal abrasion. Unexpectedly, as shown in FIG. 8B, corneal healing was not impaired compared to the control group for rabbits that received topically applied cold slurry (ECT-4143). In this group (3 rabbits), corneal healing following cold slurry treatment occurred at an average healing rate of 1.09 $mm^2$/hour in the first 24 hours following cold slurry treatment and 0.63 $mm^2$/hour between 24 hours and 60 hours following cold slurry treatment.

Figure 9:
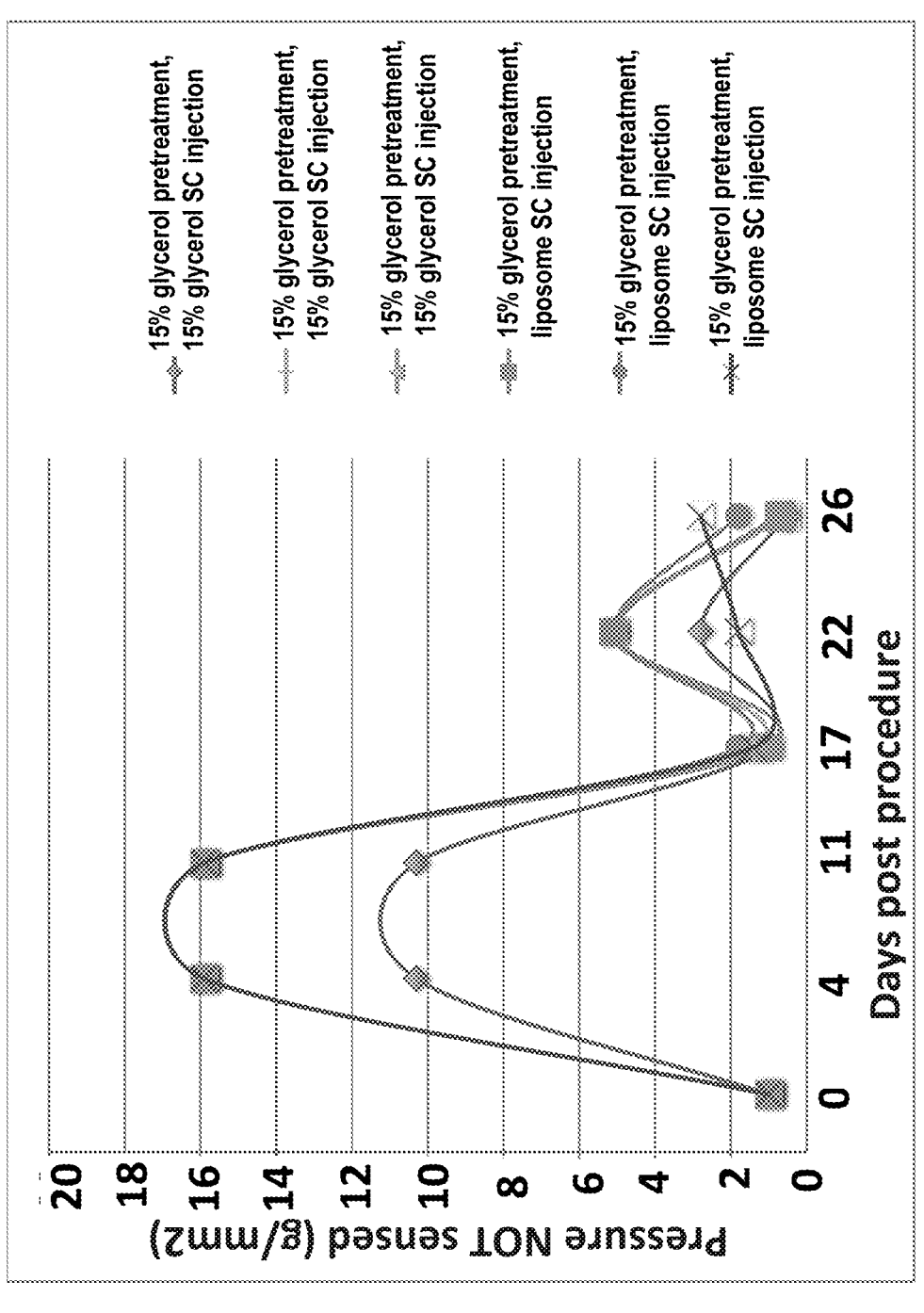
FIG. 9 is a graph showing hypesthesia in 6 rabbits' eyes over time after a combination treatment in which a cold slurry was topically applied first and then injected. In three rabbits (shown with a diamond, square, and triangle), the injected slurry did not contain liposomes, while in the other three rabbits (shown with an "X", star, and circle), the injected slurry contained liposomes.

Referring to FIG. 9, a graph shows the hypesthetic effect in 6 rabbits over time after a combination treatment in which a cold slurry was topically applied first and then injected. In 3 rabbits (shown with a diamond, square, and triangle), the topically applied cold slurry was ECT-1719 which does not contain liposomes which was followed by an injection of the same cold slurry formulation (ECT-1719). In the other 3 rabbits (shown with an "X", star, and circle), the topically applied cold slurry was again ECT-1719 (which does not contain liposomes) which was followed by an injection of cold slurry that contains liposomes (ECT-4143). The hypesthetic effect is shown as the greatest pressure to which rabbits did not produce a blink (as described herein with reference to FIGS. 6 and 7). As shown in FIG. 9, the hypesthetic effect continued to increase following treatment, likely peaking somewhere between days 4 and 11, irrespective of combination treatment (liposomal or non-liposomal injection). The hypesthetic effect tapered off returning to baseline levels at about day 17. Surprisingly, a second, less pronounced period of hypesthesia spontaneously occurred at around day 22, tapering back to baseline levels by day 26.

The data described herein support cold slurry (topical and injection) as a long-term and safe corneal numbing treatment which produces hypesthesia without permanent corneal numbering or damage.

Without being bound by any theory, the basic premise is that application of the cold slurry halts the signaling of painful stimuli by causing degeneration of the myelin sheath over the nerves. Myelin is a fatty, lipid-rich substance that allows electrical stimuli to travel down the nerve axon in a quick and efficient manner. With the administration of cold slurry over both the free nerve endings and myelinated portion of the nerves, the cold temperature will freeze or crystallize the lipid component of fat cells, inducing apoptosis, and degenerating the myelin sheath, a process known as Wallerian degeneration. This process will significantly reduce ciliary nerves from conducting painful stimuli from the cornea to the brain stem. Due to the sheer volume of distal nerve endings on the ocular surface, not all peripheral nerves are affected, therefore not all sensation from the ocular surface is eliminated, thus inducing relative hypesthesia instead of complete anesthesia. Furthermore, the effect regresses after approximately 4-8 weeks at which time ocular sensation is fully restored. Other options that induce Wallerian degeneration include radiofrequency ablation and cryoneurolysis (freezing at temperatures approaching −80° C.), but these procedures pose the risk of damaging surrounding tissue and structures. Furthermore, an inactive vehicle containing ice crystals will not harm other components of the eye, making it a reasonable application for treating nerves that lead to ocular surface pain. This approach preserves sight and normal function of the ocular surface.

Without being bound by a specific theory, injection into the subconjunctival space surrounding the corneal limbus distributes the cold slurry around the free nerve endings of the ciliary nerves. There are two main ciliary nerves that have free nerve endings branching into the corneas of each eye. Each ciliary nerve is myelinated along its axon, which is located downstream from the free nerve endings in the cornea. The injection of the cold slurry spreads downstream to where the axon of the ciliary nerve is myelinated. As the cold slurry spreads to the axons of the ciliary nerves, it causes crystallization and apoptosis of the myelin sheath, thus demyelinating the ciliary nerves. The demyelination prevents the nerves from transmitting pain signals to the brain. Alternatively, the cold slurry can cause Wallerian degeneration of the nerve and similarly prevent pain signals from being transmitted to the brain.

The topically applied and/or injected cold slurry is advantageous over other methods of administration because it does not damage the surface of the cornea.

The systems and methods disclosed herein are not to be limited in scope to the specific embodiments described herein. Indeed, various modifications of the devices, systems, and methods in addition to those described will become apparent to those of skill in the art from the foregoing description.

Example 1—In Vivo Testing of Cold Slurry Treatment for Corneal Numbing

The results of the studies described in this Example can be seen in FIGS. 5-9. Preclinical testing with animal studies was performed to determine the efficacy of the therapy including investigating the best means to deliver the therapy, the duration of the therapy's effect, and any potential side effects. For ophthalmic investigations, the New Zealand white rabbits are the ideal model because their cornea and corneal innervation system are very similar to humans, and they are a standard accepted model for corneal studies in the literature.

Procedural Preparation

Animals were given a pre-anesthetic (rabbits Xylazine 1.1 mg/kg IM Buprenorphine HCL 0.01-0.05 mg/kg IM) and a pre-surgical antibiotic (Cefazolin 25-50 mg/kg IM). Animals were then anesthetized (rabbits Ketamine 33 mg/kg IM). Animals were placed on heating pad and the vitals monitored. Two drops of Proparacaine HCL 0.5% and 5% phenylephrine/0.5% tropicamide (dilating drops) were administered to the eye to be studied. Animals were put on inhalation anesthesia (isoflurane at 1.5-2% concentration) with an $O_2$ supplement.

Study Procedure

Animals were prepped and draped in the usual sterile fashion including the instillation of povidone-iodide drops onto the ocular surface. A speculum was placed, and a topical or subconjunctival injection of the slurry is performed.

Injection Administration

For evaluating the hypesthetic potential of ECT-1719, approximately 0.7 mL of cold slurry were injected around the corneal limbus into the subconjunctival space. The injected cold slurry distributes evenly, 360 degrees, around the corneal limbus due in part to pressure from the cornea, the force of the injection, and the natural potential space present. The injection procedure is repeated every 120 seconds for a total of 10 minutes.

Control animals received treatment with sterile saline (control) or treatment with a vehicle control (uncooled slurry). At the conclusion of the procedure, the eye was carefully inspected, the speculum removed, the drapes removed, and the eye washed with sterile saline. There was an additional control group that has conventional anesthetic drops applied to the cornea. All surgery is on the left eye only (for control purposes) and lasted about 10 minutes.

The surgical procedure described above is commonly performed in humans with injection of a variety of different agents depending on the condition (e.g. steroids, antibiotics, etc.).

Topical Administration

For evaluating the hypesthetic potential of ECT-4143, the slurry was applied topically to the ocular surface, posterior to the cornea limbus. The cornea was protected with a contact lens and the eyelids with a plastic speculum. Approximately 2-3 mL of cold slurry were applied topically every approximately 90 seconds, with approximately 2-3 ml per application, until a total treatment time of 10 minutes was reached.). At the conclusion of the procedure, the eye was carefully inspected, the speculum removed, the drapes removed, and the eye washed with sterile saline.

Post-Procedures for a Survival Animal

A Neomycin/Polymyxin/Bacitracin ophthalmic ointment was applied to the operative eye, as well as several drops of Prednisone Acetate postoperatively. Animal were removed from a surgical table and placed on a heating pad. Animals had their vitals monitored (e.g., heart rate, breathing, $SPO_2$) while waiting for recovery. Animals continued to be monitored until regaining muscle control. Animals were returned to their respective cage of origin.

Post-Surgery Animal Monitoring

Animals receive a comprehensive eye exam one day after surgery and then weekly which included a measurement of corneal sensation. A measurement of intraocular pressure was taken as well, as a beneficial lowering of intraocular pressure may be observed in animals that have undergone this therapy. Furthermore, a slit lamp exam with fluorescein staining and dilated fundus exam (i.e., eyes are dilated with 5% phenylephrine, 0.5% tropicamide) was performed. Animals were placed in restrictive cages for a few seconds while eye drops were instilled.

Effect of Administration

The effect of the administration of the cold slurry were examined using a number of techniques.

The cold slurry's numbing effect was tested using an esthesiometer. A filament was extended from the device that had a certain stiffness. The animals treated with cold slurry were able to tolerate more force from the esthesiometer than animals in the control groups. This was demonstrated by whether an animal flinches when poked in the eye with the esthesiometer filament. The test was administered multiple times over the course of the study to determine the length of the numbing effect.

The impact of the cold slurry on the eye's ability to heal was also examined. An epithelial defect on the cornea was created with a trephine and corneal brush. The injury was verified with a fluorescein stain and photodocumented. The progress of the injury was measured using fluorescein staining and measuring the size of the injury. The cold slurry did not impact the eye's ability to heal.

What is claimed is:

1. A method of causing hypesthesia of an eye of a subject, the method comprising:
   applying to at least one portion of the eye a cold slurry formulation contained within a material that is thermally conductive, such that the cold slurry formulation does not have direct contact with the at least one portion of the eye;
   wherein the cold slurry formulation includes water and a freezing point depressant and the application of the cold slurry formulation causes hypesthesia of the at least one portion of the eye for a period of time of more than about two days, and an ocular sensation of the at least one portion of the eye is restored following the period of time.

2. The method of claim 1, wherein the at least one portion of the eye comprises a sclera.

3. The method of claim 1, wherein the thermally conductive material comprises at least one of a metal and a polymer.

4. The method of claim 1, wherein a sclera of the eye of the patient is cooled to a temperature of between about −6° C. and about 4° C. during the application of the device.

5. The method of claim 1, wherein application of the cold slurry formulation directs cooling only to one or more areas of potential therapeutic effect.

6. The method of claim 1, wherein the material that is thermally conductive substantially prevents cooling of an untargeted portion of the eye, such that undesired side effects are substantially minimized.

7. The method of claim 6, wherein the undesired side effects include irritation of the eye.

8. The method of claim 1, wherein hypesthesia includes a reduction of ocular discomfort without a complete blockage of ocular sensation.

9. A method of causing hypesthesia of an eye of a subject, the method comprising:
   applying a device to at least one portion of the eye of the subject, the device comprising a thermally conductive material comprising at least one of a metal and a polymer, the device comprising a cold slurry that comprises water and a freezing point depressant,
   wherein the application of the device causes hypesthesia of the at least one portion of the eye for a period of time of more than about two days, and an ocular sensation of the at least one portion of the eye is restored following the period of time.

10. The method of claim 9, wherein the at least one portion of the eye comprises a sclera.

11. The method of claim 9, wherein the freezing point depressant is glycerol.

12. The method of claim 9, wherein a sclera of the eye of the patient is cooled to a temperature of between about −6° C. and about 4° C. during the application of the device.

13. The method of claim 9, wherein application of the cold slurry formulation directs cooling only to one or more areas of potential therapeutic effect.

14. A method of causing hypesthesia of an eye of a subject, the method comprising:

providing a device including a thermally conductive material that contains a cold slurry formulation;

applying the device including the thermally conductive material to at least one portion of the eye;

wherein the cold slurry formulation includes water and a freezing point depressant and the application of the device causes hypesthesia of the at least one portion of the eye for a period of time of more than about two days, and an ocular sensation of the at least one portion of the eye is restored following the period of time.

15. The method of claim 14, wherein the at least one portion of the eye comprises a sclera.

16. The method of claim 14, wherein the thermally conductive material comprises at least one of a metal and a polymer.

17. The method of claim 14, wherein the freezing point depressant is glycerol.

18. The method of claim 14, wherein a sclera of the eye of the patient is cooled to a temperature of between about −6° C. and about 4° C. during the application of the device.

19. The method of claim 14, wherein application of the cold slurry formulation directs cooling only to one or more areas of potential therapeutic effect.

20. The method of claim 14, wherein hypesthesia includes a reduction of ocular discomfort without a complete blockage of ocular sensation.

\* \* \* \* \*